(12) United States Patent
Monzyk et al.

(10) Patent No.: US 7,399,717 B2
(45) Date of Patent: Jul. 15, 2008

(54) OXYGEN GENERATION IN WHOLE BLOOD BY PHOTOLYTIC ACTIVATION

(75) Inventors: Bruce F. Monzyk, Delaware, OH (US); Eric C. Burckle, Dublin, OH (US)

(73) Assignee: Battelle Memorial Institute, Columbus, OH (US)

( * ) Notice: Subject to any disclaimer, the term of this patent is extended or adjusted under 35 U.S.C. 154(b) by 404 days.

(21) Appl. No.: 11/130,047

(22) Filed: May 16, 2005

(65) Prior Publication Data

US 2005/0265894 A1 Dec. 1, 2005

Related U.S. Application Data

(63) Continuation-in-part of application No. 10/485,934, filed on Sep. 7, 2004, and a continuation-in-part of application No. 10/485,455, filed on Sep. 7, 2004, and a continuation-in-part of application No. 10/485,476, filed on Jul. 26, 2004.

(60) Provisional application No. 60/571,462, filed on May 14, 2004.

(51) Int. Cl.
*A61M 37/00* (2006.01)
*A61M 1/00* (2006.01)
*C10B 25/00* (2006.01)

(52) U.S. Cl. ............... 442/45; 604/4.01; 604/6.08; 604/6.14; 422/44; 422/46; 422/47; 422/48; 202/244; 202/254

(58) Field of Classification Search ....... 604/4.01–6.16, 604/7–10, 23–25; 204/252, 244, 254; 422/44–48; 210/748–766
See application file for complete search history.

(56) References Cited

U.S. PATENT DOCUMENTS

| | | | |
|---|---|---|---|
| 3,533,408 | A | 10/1970 | Paoli |
| 4,011,149 | A | 3/1977 | Nozik |
| 4,140,591 | A | 2/1979 | Fong et al. |
| 4,244,824 | A | 1/1981 | Lange et al. |
| 4,306,018 | A | 12/1981 | Kirkpatrick |
| 4,309,463 | A | 1/1982 | Lange et al. |
| 4,381,978 | A | 5/1983 | Gratzel et al. |
| 4,466,869 | A | 8/1984 | Ayers |
| 4,478,699 | A | 10/1984 | Halmann et al. |
| 4,521,499 | A | 6/1985 | Switzer |
| 4,595,568 | A | 6/1986 | Van Damme et al. |
| 4,643,817 | A | 2/1987 | Appleby |
| 4,790,916 | A | 12/1988 | Murphy et al. |
| 4,793,910 | A | 12/1988 | Smotkin et al. |
| 4,889,604 | A | 12/1989 | Khan et al. |
| 4,952,511 | A | 8/1990 | Radmer |
| 4,968,483 | A * | 11/1990 | Muller et al. ............ 422/45 |
| 4,970,166 | A | 11/1990 | Mori |
| 5,052,382 | A | 10/1991 | Wainwright |
| 5,086,620 | A | 2/1992 | Spears |

(Continued)

FOREIGN PATENT DOCUMENTS

WO WO 01/70396 A2 9/2001

(Continued)

*Primary Examiner*—Tatyana Zalukaeva
*Assistant Examiner*—Philip Wiest
(74) *Attorney, Agent, or Firm*—Richard M. Klein; Fay Sharpe LLP

(57) ABSTRACT

Apparatus and methods for photolytic oxygenation of whole blood.

21 Claims, 7 Drawing Sheets

U.S. PATENT DOCUMENTS

| | | |
|---|---|---|
| 5,174,877 A | 12/1992 | Cooper et al. |
| 5,262,023 A | 11/1993 | Sayama et al. |
| 5,294,315 A | 3/1994 | Cooper et al. |
| 5,294,401 A | 3/1994 | Hagiwara |
| 5,366,696 A | 11/1994 | Williams |
| 5,614,378 A * | 3/1997 | Yang et al. .................... 435/41 |
| 5,779,912 A * | 7/1998 | Gonzalez-Martin et al. . 210/748 |
| 5,865,960 A | 2/1999 | Park et al. |
| 5,964,725 A | 10/1999 | Sato et al. |
| 6,042,875 A | 3/2000 | Ding et al. |
| 6,051,194 A | 4/2000 | Peill et al. |
| 6,136,186 A | 10/2000 | Gonzalez-Martin et al. |
| 6,183,695 B1 | 2/2001 | Godec et al. |
| 6,335,122 B1 * | 1/2002 | Yamada et al. ........... 429/231.4 |

FOREIGN PATENT DOCUMENTS

| | | |
|---|---|---|
| WO | WO 01/70396 A3 | 9/2001 |

* cited by examiner

US 7,399,717 B2

OXYGEN GENERATION IN WHOLE BLOOD BY PHOTOLYTIC ACTIVATION

RELATED APPLICATIONS

The present application claims priority to U.S. Provisional Application Ser. No. 60/571,462, filed on May 14, 2004, and is a continuation-in-part of U.S. patent application Ser. No. 10/485,455 filed Sep. 7, 2004; Ser. No. 10/485,476 filed Jul. 26, 2004; and, Ser. No. 10/485,934 filed Sep. 7, 2004. The disclosures of all of the above applications are incorporated herein by reference.

BACKGROUND

The present disclosure, in various embodiments, is directed to a photolytic apparatus that utilizes light energy to achieve physiological gas exchange in whole blood, such as in the blood stream of a patient experiencing respiratory difficulties, whole blood utilized to transport organs, etc., and to a photolytic cell or module used for the same. The disclosure finds particular applications in conjunction with the field of artificial organs and the medical arts. However, it is to be appreciated, that the embodiment disclosed herein will also find applications in related fields due to the photo-electro chemical transformations involved therein.

In this regard, despite major reduction in disease mortality experienced over the past several decades, the mortality associated with chronic lung disease has continued to rise. This is largely due to a lack of emerging treatments, and inadequate technology for providing intermediate ("bridge" therapy) or long-term respiratory support. Numerous technical solutions have been proposed and implemented. Moreno-Cabral R J, Dembitsky W P, Adamson R M, Daily P O., *Percutaneous extracorporeal membrane oxygenation. Adv Card Surg*, 5: 163-179, 1994; Funakubo A, Higami T, Sakuma I, Fukui Y, Kawamura T, Sato K, Sueoka A, Nose Y., *Development of a membrane oxygenator for EXMO using a novel fine silicone hollow fiber, ASAIO,* 42: M837-840, 1996; Naganuma S, Nitta S, Yambe T, Kobayashi S, Tanaka M, Hashimoto H., *Gas exchange efficiency of a membrane oxygenator with use of a vibrating flow pump, Artif Organs,* 19: 747-749, 1995; Yamane S, Ohashi Y, Sueoka A, Sato K, Kuwana J, Nose Y., *Development of a silicone hollow fiber membrane oxygenator for ECMO application, ASAIO,* 44: M384387, 1998; Stammers A H, Fristoe L W, Alonso A, Song Z, Galbraith T., *Clinical evaluation of a new generation membrane oxygenator a prospective randomized study, Perfusion,* 13: 165-175, 1998; Kitano Y, Takata M, Miyasaka K, Sasaki N, Zhang Q, Liu D, Tsuchida Y., *Evaluation of an extracorporeal membrane oxygenation system using a nonporous membrane oxygenator and a new method for heparin coating, J Pediatric Surgery,* 32: 691-697, 1997; Sueda T, Fukunmaga S, Morita S, Sueshiro M, Hirai S, Okada K, Orihashi K, Matsuura Y., *Development of an intravascular pumping oxygenator using a new silicone membrane, Artif Organs,* 21: 75-78, 1997; Mortensen J D, Berry G., *Conceptual and design features of a practical, clinically effective intravenous mechanical blood oxygen/carbon dioxide exchange device (IVOX), Int J Artif Organs,* 12: 384-389, 1989; and, Babley B, Bagley A, Henrie J, Fooerer C, Brohamer, J, Burkart J, Mortensen J D., *Quantitative gas transfer into and out of circulating venous blood by means of an infra-vena caval Oxygenator, ASAIO Trans,* 37: M413-415, 1991. However, none are believed, to this point, to provide sufficient yield, safety, and ease of use to support broad clinical deployment.

Furthermore, numerous improvements in lung transplantation have occurred due to advances in procurement, preservation, and implantation. Stammers A H, Fristoe L W, Alonso A, Song Z, Galbraith T., *Clinical evaluation of a new generation membrane oxygenator a prospective randomized study, Perfusion,* 13: 165-175, 1998; Kitano Y, Takata M, Miyasaka K, Sasaki N, Zhang Q, Liu D, Tsuchida Y., *Evaluation of an extracorporeal membrane oxygenation system using a non-porous membrane oxygenator and a new method for heparin coating, J Pediatric Surgery,* 32: 691-697, 1997; Sueda T, Fukunmaga S, Morita S, Sueshiro M, Hirai S, Okada K, Orihashi K, Matsuura Y., *Development of an intravascular pumping oxygenator using a new silicone membrane, Artif Organs,* 21: 75-78, 1997; and, Mortensen J D, Berry G., *Conceptual and design features of a practical, clinically effective intravenous mechanical blood oxygen/carbon dioxide exchange device (IVOX), Int J Artif Organs,* 12: 384-389, 1989. However, the large discrepancy between the numbers of donors and recipients, the low yield of usable lungs, and the absence of temporizing methods for patients awaiting transplantation, make this option outside the reach of many patients.

Prior artificial lung technologies have been based on the delivery to the bloodstream of oxygen gas via hollow fibers, followed by back-and-forth diffusion across permeable membranes. Golob J F, Federspiel W J, Merrill T L, Frankowski B J, Kitwak K, Russian H, Hattler B G., *Acute in vivo testing of an intravascular respiratory support catheter, ASAIO J,* 47: 434437, 2001; Federspiel W J, Hewitt T J, Hattler B G., *Experimental evaluation of a model for oxygen exchange in a pulsating intravascular artificial lung, Ann Biomed Eng,* 28: 160-167, 2000; and, Swischenberger J B, Anderson C M, Cook K E, Lick S D, Mockros L H, Bartlett R H., *Development of an implantable artificial lung: challenges and progress, ASAIO J.* 47: 316-20, 2001. These systems are attractive since gas exchange, analogous to that of the normal lung, is reliant on diffusivity and differential gas pressure on opposite sides of the membrane to drive $O_2/CO_2$ exchange. The principal weakness, however, of these systems is that they require the presence of major diffusion boundary layers, which results in slowed mass transport and the need for a large surface area to achieve sufficient flux of gases. In addition, these systems require a continuous source of exogenous pressurized $O_2$ gas, generally via a tank or system of tanks.

The present disclosure seeks to circumvent one or more of the limitations set forth above by considering the problem of intravascular oxygenation from a fundamentally different perspective. Rather than delivering oxygen gas to the blood (or removing carbon dioxide against a back pressure of $O_2$), the present disclosure uses photolytic energy to generate dissolved oxygen directly from the water already present in the blood, thereby eliminating the need for exogenous gas delivery, gas or liquid selective diffusion boundary layers, and the requirement for operating at or near equilibrium (FIG. 1.). This approach thus constitutes a direct mechanism by which photolytically driven oxygenation of whole blood can occur.

It has previously been shown by Applicants that it is possible to generate dissolved oxygen directly from the water content of synthetic serum, based on the interaction of UV light with a semi-conducting titanium dioxide thin film. Dasse K A, Monzyk B F, Burckle E C, Busch J R, Gilbert R J., *Development of a photolytic artificial lung, Preliminary concept validation, ASAIO Journal,* 48:556-563, 2003. The optoelectronic interaction of a metal chelate chromophores with transition metal oxides is believed to be the basis for the well known phenomenon in nature, the light-dependent oxygen generation occurring in photosynthetic (PS) organisms, cyanobacteria, and, higher plants and algae. Limburg J, Vrettos J S, Liable-Sands L M, Rheingold A L, Crabtree R H, Bredvig G W., *A functional model of O—O bond formation by the O$_2$-evolving complex in photosystem II, Science,* 283: 1524-1527, 1999; Vrettos J S, Brudvig G W., *Water oxidation chemistry of photosystem II, Philos Trans Royal Society of London B Biol Sci,* 357: 1395-1404, 2002; Yachandra V K, DeRose V J, Latimer M J, Mukerji I, Sauer K, Klein M P., *Where plants make oxygen: a structural model for the photosynthetic oxygen-evolving manganese cluster, Science,* 260: 675-679, 1993; and, Yachandra V K, Sauer K, Klein M P., *Manganese cluster in photosynthesis: Where plants oxidize water to dioxygen, Chem Rev,* 96: 2927-2950, 1996. The proposed photolytic lung technology disclosed herein thus builds upon the known ability of the metal oxide, the anatase form of titanium dioxide, $TiO_2$, to serve both as the chromophore and the charge separation center. Fernandez-Ibanez P, Blanco J, Malato S, de las Nieves F J., *Application of the colloidal stability of TiO$_2$ particles for recovery and reuse in solar photocatalysis, Water Res.* 37(13):3180-8, 2003; Topoglidis E, Campbell C J, Palomares E, Durrant J R., *Photoelectrochemical study of Zn cytochrome-c immobilized on a nanoporous metal oxide electrode, Chem Commun (Camb).* 21; (14): 1518-9, 2002; Hagfeldt A, Gratzel M., *Molecular photovoltaics, Acc Chem Res.* 33(5):269-77, 2000; and, Tsai P, We C T, Lee C S., *Electrokinetic studies of inorganic coated capillaries, J Chromatography B Biomed Appl.* 657(2):285-90, 1994. The present disclosure describes and provides for the generation of dissolved oxygen, and the resulting increase of oxyhemoglobin, via photolytic means, in whole mammalian blood.

BRIEF DESCRIPTION

Disclosed herein, in various embodiments, is a process and apparatus for using photolytic energy to generate dissolved oxygen from whole blood, thus providing an increase of oxyhemoglobin as a function of the metal oxide (i.e., $TiO_2$) surface illumination. In one embodiment, the disclosure includes flowing mixed arterial-venous whole blood in a recirculating loop in a device having a nanocrystalline metal oxide $TiO_2$ thin film. Following light exposure of the metal oxide or $TiO_2$ film only (while not exposing the blood to the light), the fraction of oxy-hemoglobin in the blood rapidly increases and remains substantially stable thereafter. The fraction of dissolved oxygen contained in the serum phase of the blood increases in a parallel manner with oxyhemoglobin as a result of light induction, indicating that near complete oxygenation of the blood's hemoglobin content has been achieved. The present disclosure demonstrates that it is feasible to photolytically oxygenate the hemoglobin contained in whole blood with oxygen derived from the blood's own water content by only providing energy at mild conditions.

In another embodiment, the present disclosure is directed to a process and a photolytic apparatus or device for oxygenating whole blood. The device has a photolytic cell having a photo-reactive surface. The photo-reactive surface comprises a light-activated catalyst and a disproportionate catalyst which converts water in the whole blood into dissolved oxygen upon light activation.

In this regard, the photo-reactive surface comprises a light transparent substrate and a photolytic coating. The photolytic coating comprises a layer of light-activated catalyst and a layer of disproportionate catalyst. The light-activated catalyst converts, when photo irradiated, water ($H_2O$) in the blood into hydrogen ions, electrons and active oxygen. The hydrogen ions formed during photolysis can be removed or reacted with carbonate ions in the whole blood to form carbonic acid. The carbonic acid then reacts with carbonic anhydrase in the blood to form water and carbon dioxide which is subsequently removed. The active oxygen formed during photolysis is then converted by a disproportionate catalyst (such as $MnO_2$, etc.) into dissolved oxygen. The electrons generated during photolysis are subsequently electrically conducted away to avoid reversal of the conversion reaction. This results in the oxygenation of whole blood without the need of exogenous gas delivery, etc.

In a further embodiment, the disclosure relates to a process and device for enhancing the viability of an organ to be transplanted. The process comprises adding to an organ to be transplanted and/or transported whole blood. The whole blood is then oxygenated. This is by a photolytical device which generates dissolved oxygen, and a resulting increase in oxyhemoglobin, from water present in the whole blood by photolytic means.

These and other non-limiting characteristics of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 4A shows a general illustration of the photolytic artificial lung connected externally to a patient. FIG. 4B shows an interior view of the components of one embodiment of the photolytic device. FIG. 4C also shows an inside view of an alternative embodiment of the photolytic device, and FIG. 4D illustrates the chemical reactions occurring therein.

DETAILED DESCRIPTION

Figure 1:
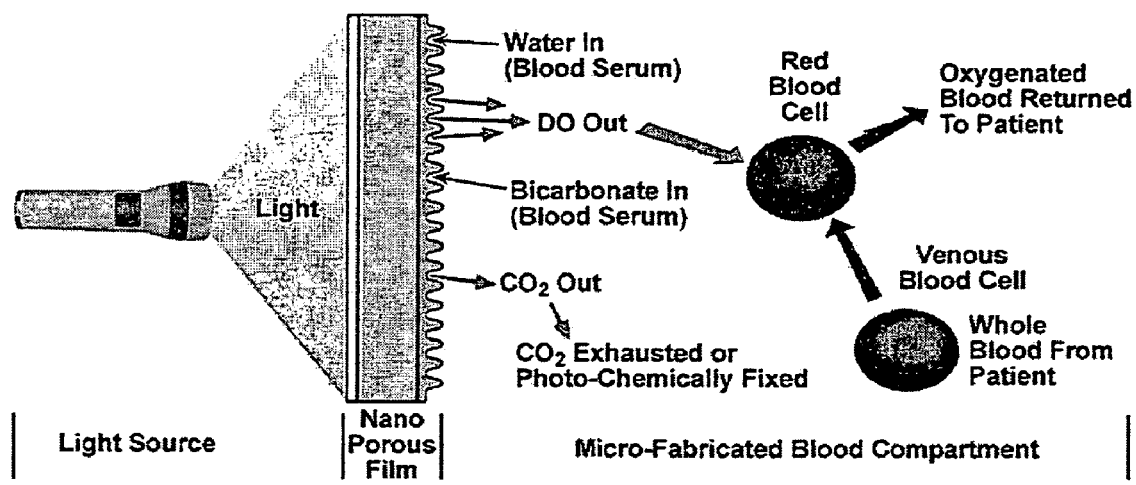
FIG. 1 is a diagram showing the fundamental mechanism of a photolytic cell or chamber. The photolytic technology is based on the ability of transition metal oxides to convert light energy to electric current; the resulting charge separation is used to generate oxygen from adjacent (non diffusion) water molecules supplied from serum. The photochemical materials are designed to produce dissolved oxygen directly in an aqueous fluid (blood), without involving the gaseous phase, which is freely available for binding with hemoglobin. The photolytic technology utilizes a semi-conducting metal oxide material, such as $TiO_2$, $WO_3$, ZnO, or combinations thereof. Those skilled in the art will appreciate that various dopants can be added to the metal oxide layer. The light energy produces charge separation (electron-hole pairs) in the semiconductor, which results in the production of active oxygen, hydrogen ions and free electrons. DO stands for dissolved oxygen.

The unrelenting nature of chronic lung disease has long energized the pulmonary community to seek technologies to replicate the capacity of the lungs to exchange oxygen for carbon dioxide. While most such artificial lung technologies work by delivering pressurized oxygen gas to the blood through a system of hollow fibers or tubes, the present disclosure employs photolytic energy to generate dissolved oxygen in blood directly from the water already present in blood, thus eliminating the need for gas delivery.

In one embodiment, the present disclosure is directed to the use of the photolytic cell in a novel respiratory assist device and process. The respiratory assist device includes one or more photolytic cells having photochemically active material and associated components for the production of oxygen and, optionally, the regulation of pH, the removal of carbon dioxide, and the co-production of electrical energy in whole blood. The electrical energy can be used to produce additional chemical changes or reactions. The embodiment may include a photolytic chamber to house or hold a sufficient number of stacked or assembled photolytic cells to perform the rate of gas exchange desired.

The respiratory assist device can be an extracorporeal device, or a highly miniaturized, intracorporeal device, capable of achieving physiological gas exchange in patients. Utilizing the device, oxygen is photolytically generated from water in whole blood at a catalyst center, using photolytic energy under mild conditions of pressure, temperature and pH, while releasing hydrogen ions. Hydrogen ions, which may be removed or released into solutions of bicarbonate ion, present in the blood, cause conversion of these ions into carbonic acid, which spontaneously dissociates into water and $CO_2$ in the presence of carbonic anhydrase, a natural component of blood.

In another embodiment, a semi-conducting metal oxide is utilized as the photo-absorption element, such as the anatase form of titania, or $TiO_2$. Photolysis of this oxide results in the generation of active oxygen in whole blood. The light energy associated with activation by a light source, such as a 354 nm UV laser light, selectively excites the $TiO_2$ semiconductor electronic transition (350-389 nm band, or about 3.2 eV) with minimal wasted radiation or transmission. Special dopants may adjust this wavelength, in order to reduce the energy requirement and even to allow activation within the range of visible light. UV energy produces charge separation in the anatase, which then produces active oxygen and free electrons, the latter being electrically conducted away. Diffusion layers are minimized through the use of electron conductance to and from the photolytic site (as is done in natural photosynthesis) by photolytic transparency and by electrochemical conduction. The active oxygen is then converted to dissolve oxygen through the use of a disproportionation catalyst such as $MnO_2$.

Preferably, the device comprises a blood inlet cannula, a pump, at least one photolytic cell, a light source that irradiates the photolytic cells, an oxygenated blood outlet cannula and an optional carbon dioxide vent and/or absorption device. A power source and/or batteries can be present to power the pump or light source. One or more in-line sensors and processors can be present to monitor and optimize the blood flow through the system, the amount of oxygen and/or carbon dioxide generation, the presence of toxins, etc. Desaturated blood circulating through the device will be pumped through the photolytic cells where light activation will result in dissolved oxygen generation and, in some embodiments, carbon dioxide removal.

A more complete understanding of the components, processes and apparatuses disclosed herein can be obtained by reference to the accompanying drawings. These figures are merely schematic representations based on convenience and the ease of demonstrating the present development, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 3:
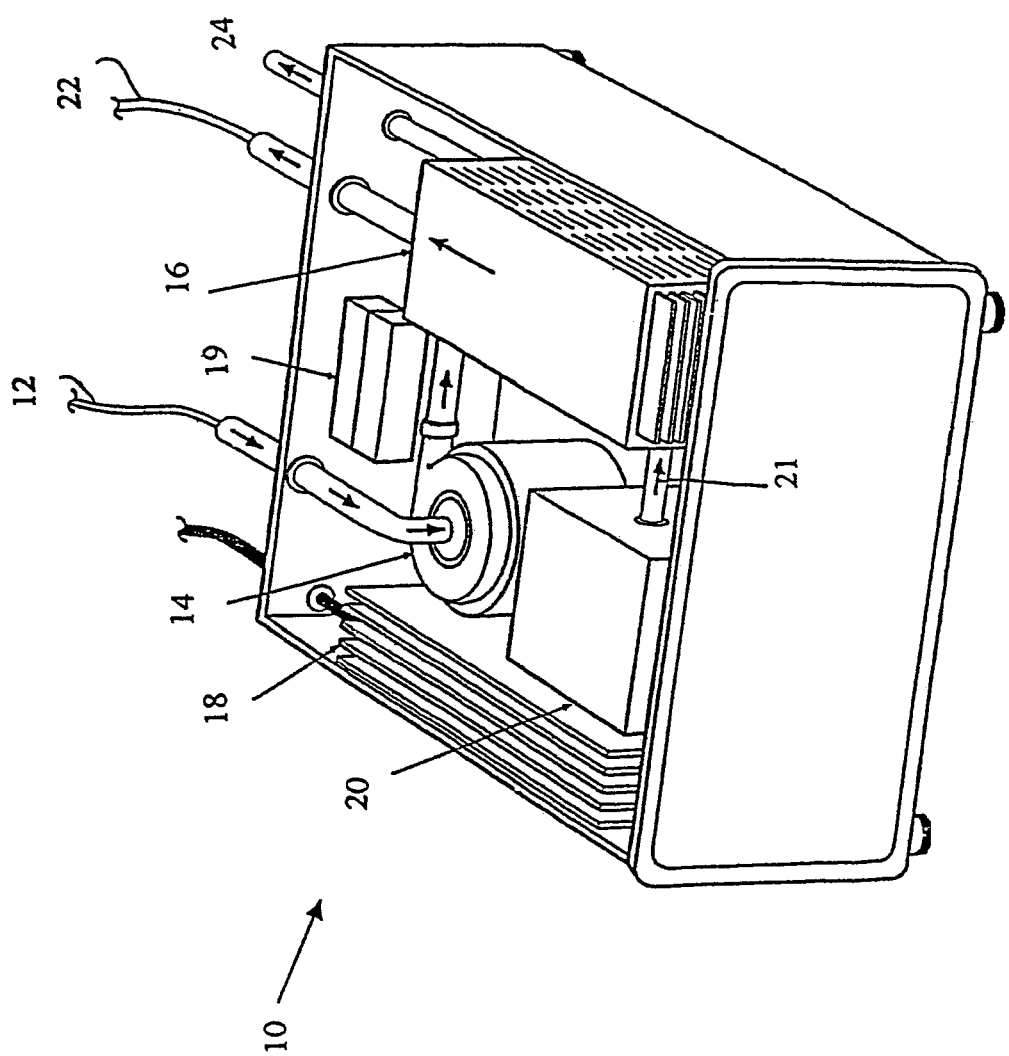
FIG. 3 shows a perspective view of an embodiment of a photolytic device for oxygenated whole blood designed for external or extra-corporeal usage.

More particularly, FIG. 3 shows an embodiment of a device 10 developed as an extra-corporeal respiratory assist system. The device 10 includes a blood inlet 12 that cannulates blood from the patient into the device 10. The blood inlet 12 is connected to a pump 14 that draws blood from the patient into the device 10. The pump 14 directs desaturated blood through one or more photolytic cells 16 where light activation (for example, laser at 350-390 nm) results in oxygen generation and ultimate carbon dioxide removal via a carbon dioxide sorption device 24 or external ventilation. A power supply 18 or optional battery 19 activates the light source 20. The light source 20 emits light photos 21 which irradiate the photolytic cells 16. In turn, the photolytic cells 16 photochemically initiate a series of chemical reactions that produce oxygen and remove carbon dioxide from the blood. Oxygenated blood travels from the artificial lung 10 back to the patient by way of a blood outlet 22. Consequently, the artificial lung 10 takes blood from the venous circulation of a patient and returns it to the arterial circulation.

The device omits the gaseous state that causes problems which have limited other blood oxygenation technologies, while optionally consuming carbon dioxide. Also, the device does not require the careful control of temperature or pressure. As briefly mentioned above, the materials for use in the present photolytic device are generally biocompatible and prevent blood contamination. Blood contact with the coatings is also minimized. Diffusion layers, which can decrease oxygenation rates, are minimized using electrical conduction of electrons and cations to and from the photolytic site by incorporating thin films having good photolytic transparency, and electrical and electrochemical conduction.

The wave length, beam size, pulse duration, frequency and fluency of the light source are adjusted to produce maximum and/or efficient gas exchange. Similarly, pump rate, flow-through capacity, etc. of the photolytic cells are also so adjusted. This can be accomplished by sensors and regulators which also monitor reaction chemistry, toxins, etc. The sensors and regulators have the capacity to auto-regulate various parameters of the system in response to the conditions monitored by the sensors.

The photolytic device can be designed so that it is an extra corporeal device or an intra-corporeal device. For example, the photolytic device can be designed as a miniaturized, implantable unit. Such a unit is configured to be implantable and it uses a transcutaneous energy transmission system and/or an internal light source for energy conversion.

Figure 4A:
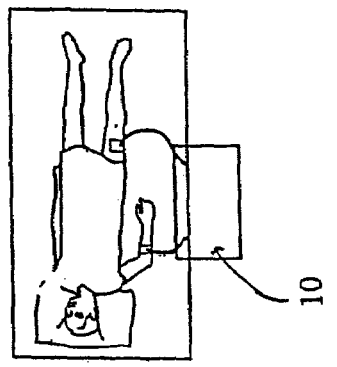
FIGS. 4A-4D illustrate the various embodiments of the photolytic device set forth in FIG. 3.
Figure 4B:
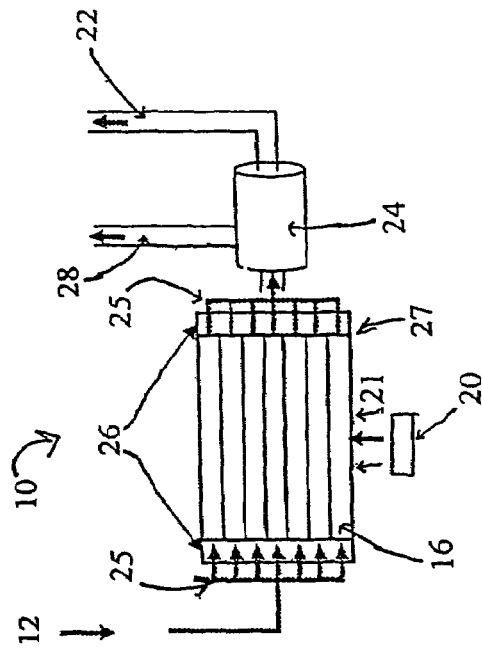
Figure 4C:
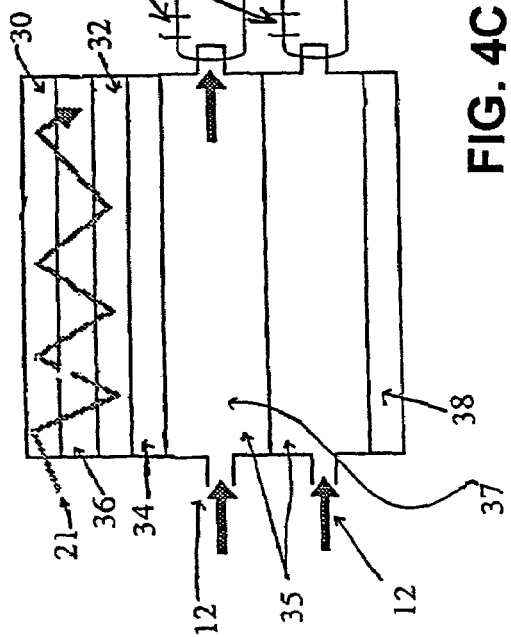
Figure 4D:
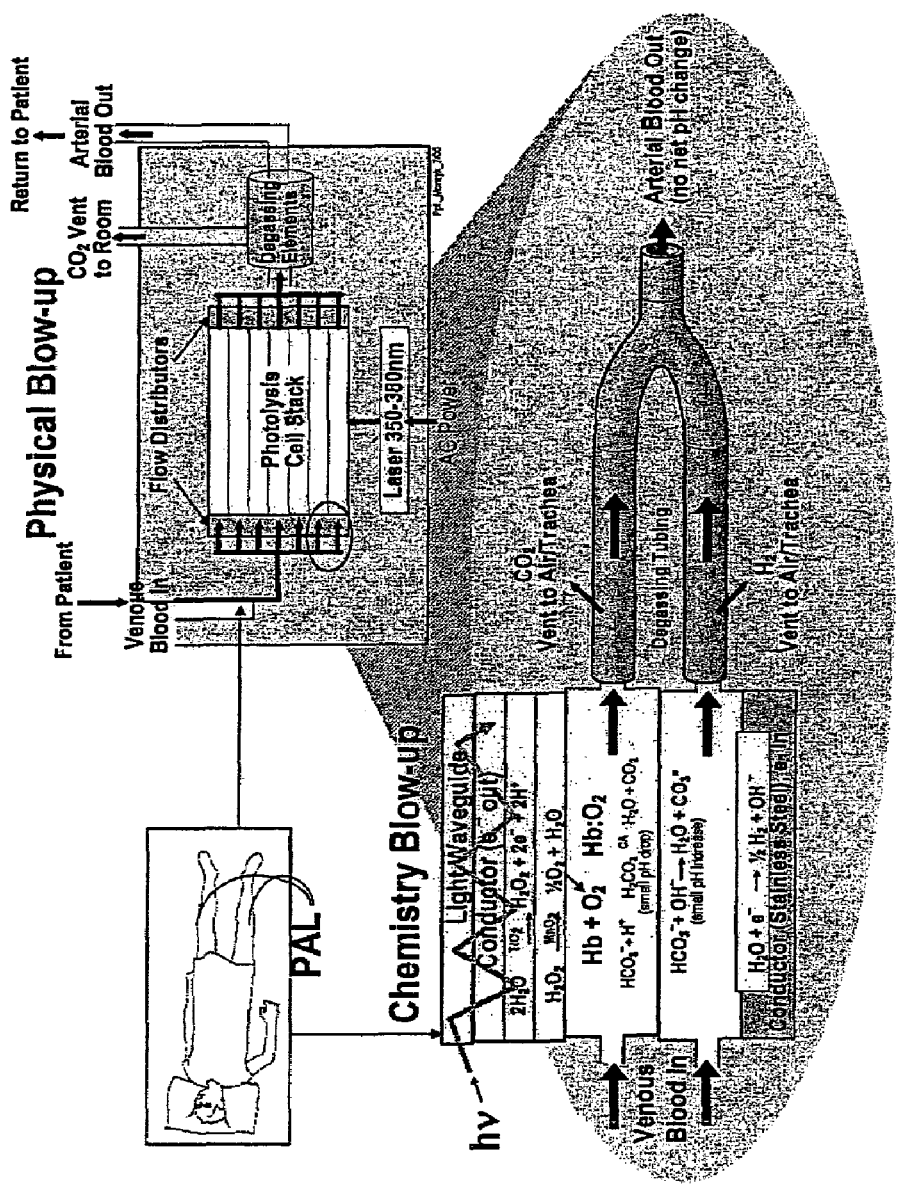

FIG. 4A shows a simple representation of a patient attached to a device 10 as an extra-corporal device. Most preferably, the device is designed to provide at least about 150 ml of dissolved oxygen per minute at 5 L/min of blood flow through the system for a human patient. FIGS. 4B and 4C are enlargement views showing the components of various embodiments of the device 10. FIG. 4D shows the chemical transformations which occur in each compartment of the various embodiments of the device.

The device 10 pumps venous blood from the patient through a blood inlet 12. The venous blood enters by means of a flow distributor 25 into one or more photolytic cell(s) 16. The photolytic cell(s) may be optionally arranged to form a stack of photolysis cells 27. The amount of blood entering and leaving the photolytic cell(s) 16 is controlled by flow distributor 25. See FIG. 4B.

A light source 20 irradiates the photolytic cell(s) 16, thereby initiating the photochemical reactions within the photolytic cell(s) 16 that ultimately form dissolved oxygen that binds to blood hemoglobin (Hb). Excess carbon dioxide and hydrogen formed from the chemical reactions in the photolytic cell(s) 16 enter one or more gas sorption devices 24 for storage and/or eventual venting through a venting outlet 28. Once the blood has been oxygenated, and the carbon dioxide removed, the blood returns to the artery of a patient by way of blood outlet 22. Among the components of the photolytic device not illustrated in this embodiment is the blood pump, power supply, control electronics and sensory technology for monitoring reaction chemistry, the amount of oxygen, carbon dioxide, etc. generated the presence of potential toxins, etc.

The main component of the device is the photolytic cell 16. See, for example, FIG. 4C. Light energy 21 from a light source 20 enters the photolytic cell 16 through a transparent substrate or window 30 and activates a layer of light-activated catalyst 32. As discussed in more detail below, an example of such a light activated catalyst is anatase ($TiO_2$). Depending on the catalyst 32 used, the light-activated catalyst 32 converts water in the blood into intermediate active oxygen, hydrogen ions and excess electrons, or directly converts water into dissolved oxygen. An optional second catalyst, i.e. a disproportionation catalyst, 34 can be used to convert the intermediate active oxygen to dissolved oxygen, $O_2$. An example of such a second catalyst is manganese dioxide ($MnO_2$). Excess electrons are formed during the conversion of water to dissolved oxygen and are conducted out from the catalyst 32 to an anode conductor layer 36 such as gold or titanium metal film. In chamber 37, the dissolved oxygen binds to hemoglobin (Hb) in the blood and the oxygenated blood returns to the patient via an arterial blood outlet 22.

Additionally, in chamber 37, bicarbonate ions which are also present in the deoxygenated blood react with the hydrogen ions generated above to form carbonic acid. The carbonic acid is then converted to water and carbon dioxide by carbonic anhydrase. The water formed reacts with electrons at the cathode 38 to form hydrogen gas ($H_2$) and hydroxyl groups. The hemoglobin also releases carbon dioxide when the oxygen binds to the hemoglobin. The excess carbon dioxide and hydrogen created from the reactions occurring in the photolytic cell 16 enter one or more gas sorption devices 24 for storage or venting.

Figure 5:
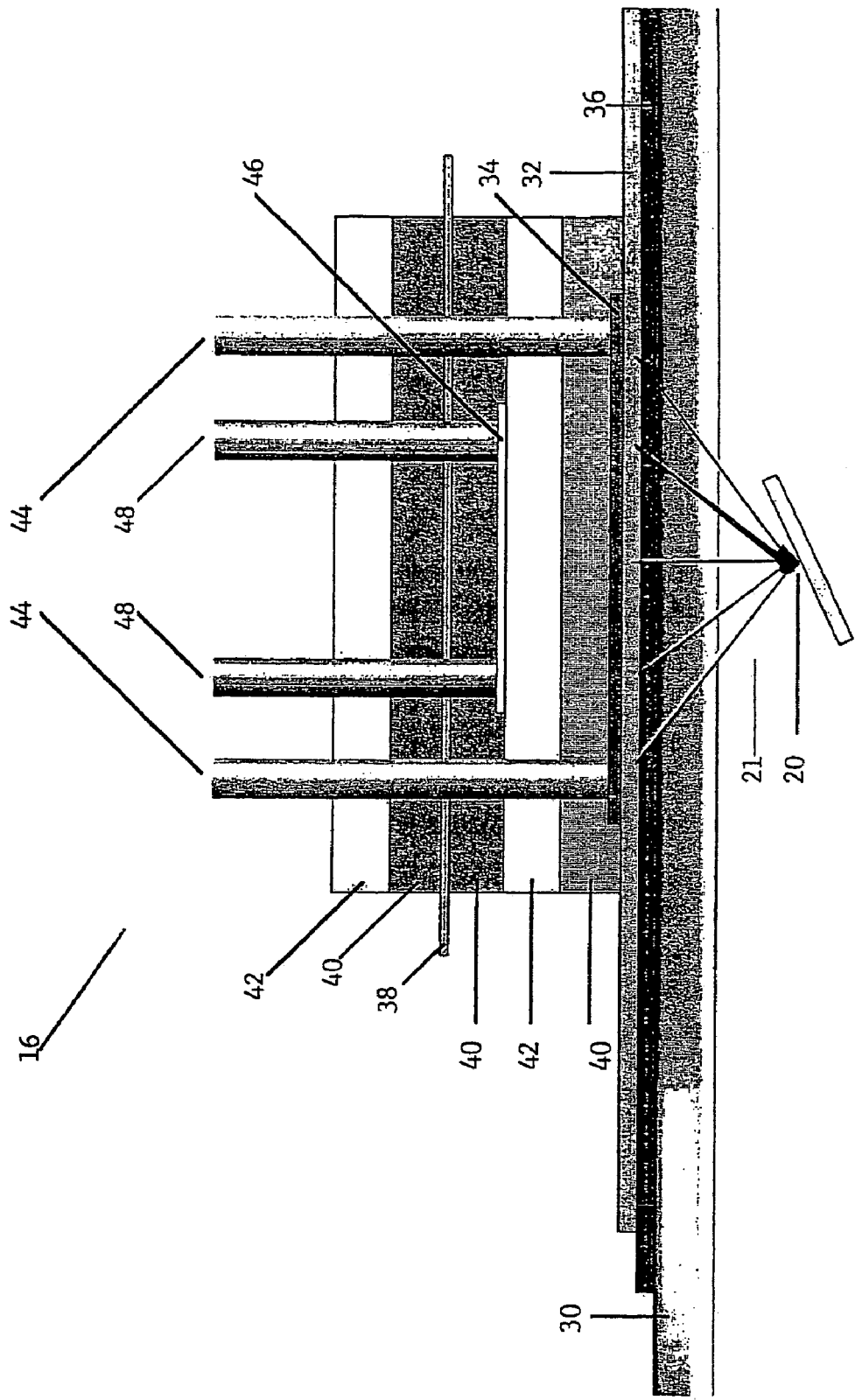
FIG. 5 shows a schematic view of the model photolytic cell apparatus. Among other things, this view depicts the relative positions of the coated test surface, light source, and the chemical sensor in place to monitor the chemical yield of the system.

FIG. 5 shows a flow-through embodiment of the photolytic cell 16. In the flow-through cell embodiment, the following main components of the photolytic cell 16 are assembled, i.e. a conductive coating of vacuum deposited Ti metal 36, a coating of adherent $TiO_2$ (anatase) 32, an optional $MnO_2$ particulate layer 34, and then tested using a bicarbonate solution. A UV laser light 20 was shown on the transparent glass or quartz substrate 30 so to initiate the reactions. As discussed below, this cell was utilized to collect pH and data as a function of laser U.V. irradiation demonstrating the effectiveness of the disclosure.

In this regard, the photolytic cell 16 of FIG. 5 includes a transparent window 30 or wave guide for the entry of light energy in the form of photons 21 from a light source 20 such as an ultraviolet laser light. On one side of the glass slide is an anode conductor layer 36, such as titanium (Ti) metal film. Attached to the anode conductor layer 36, is a layer of a light activated catalyst 32 such as anatase ($TiO_2$). An optional catalyst layer 34, such as manganese dioxide, is adjacent to the light activated catalyst layer 32. The photolytic cell 16 includes one or more layers of silicone gaskets or spacers 40 and an acrylic housing 42. A pair of anolytes 44 (in/out) is connected to the light activated catalyst layer 32 or optional catalyst layer 34 and extend through the photolytic cell 16 away from the transparent window 30. The photolytic cell 16 further includes a cation exchange member 46, such as a NAFION® membrane from DuPont. A pair of catholytes 48 (in/out) is connected to the cation exchange member 46 and extends outwardly through the photolytic cell 16 generally away from the transparent window 30. The photolytic cell 16 further includes a cathode layer 38, such as Pt foil, adjacent to the cation exchange member 46.

Figure 6:
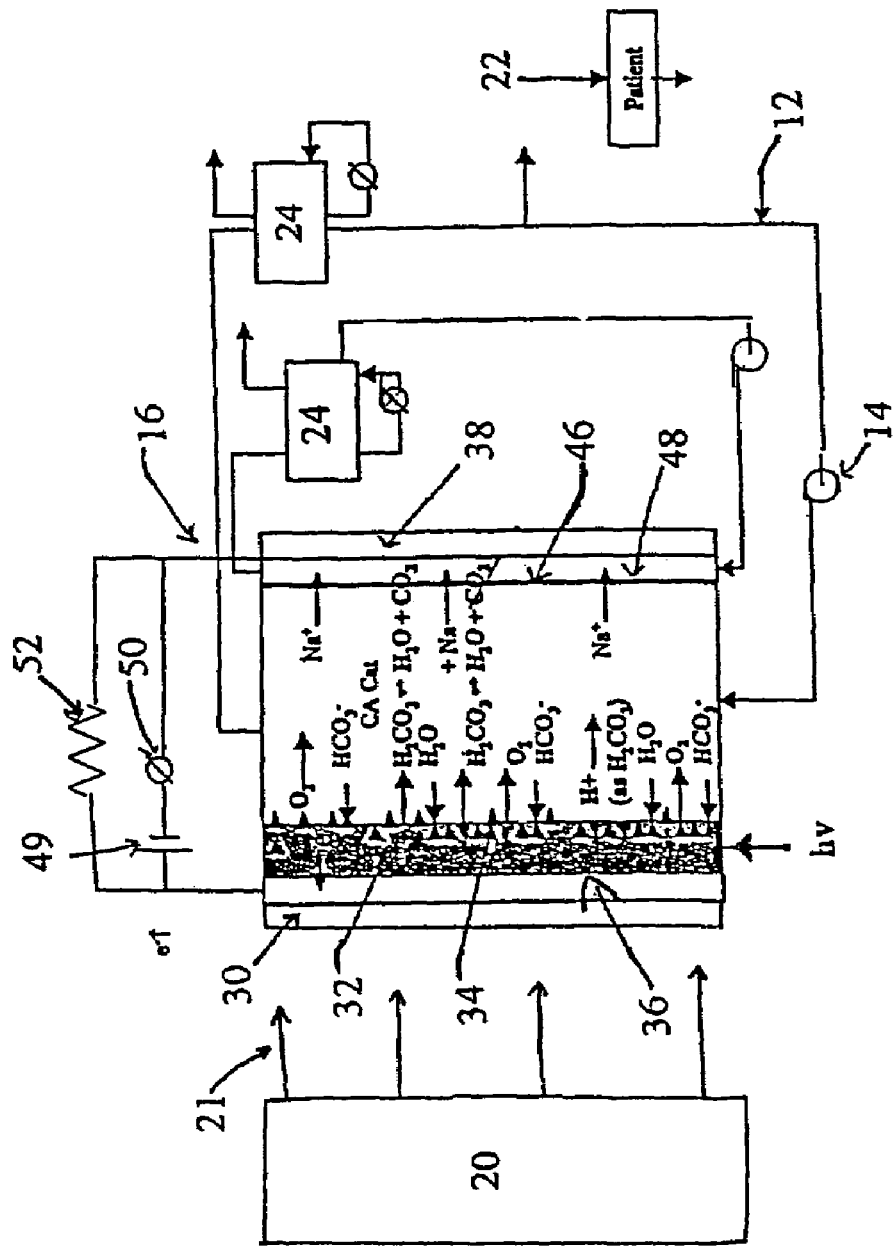
FIG. 6 shows an overall schematic diagram of the photolytic device disclosed herein.

FIG. 6 is a schematic drawing showing the electrical and chemical transformations which occur in the photolytic cell 16 of the device 10. Venous blood (low in oxygen and high in carbon dioxide) from a patient enters the photolytic cell 16 through inlet 12 by way of a peristaltic pump 14. Light photons (hv) 21 generated by light source 20 enter through a transparent window 30 or waveguide and activate the light activated catalyst 32 such as 100 μm $TiO_2$ (anatase). The light activated catalyst 32 either directly converts water to dissolved oxygen or converts water to active oxygen and hydrogen ions and an optional second catalyst 34, such as manganese dioxide ($MnO_2$) on a porous film, converts active oxygen (e.g. $H_2O_2$) into dissolved oxygen (DO). The dissolved oxygen then binds to hemoglobin present in the blood.

The electrons released from the conversion of water to oxygen are collected in an anode conductor layer 36. An optional electrical bias voltage formed from a battery 49 facilitates electron flow from the layer 36 to the cathode 38 (such as stainless steel, copper, graphite or nickel), so that the electrons do not react with the active oxygen to cause a back reaction and the reformation of water.

The electrical current and electron flow can be regulated by a current regulator 50 or resistor 52. The electrons can react with water to form hydrogen gas, $H_2$, and a hydroxyl ion (OH−). The hydrogen gas formed is moved to a gas sorption device, where it is stored and/or released (i.e., expired). Sodium ($Na^+$) ions from the blood migrate across the cation exchange membrane 46 and react with hydroxyl ions to form sodium hydroxide (NaOH) in the catholyte 48. The hydrogen ions formed from the conversion of water at the light activated catalyst reacts with bicarbonate ions to form carbonic acid, which is converted by carbonic anhydrase enzyme present in the blood or added to form carbon dioxide and water. The carbon dioxide formed in the photolytic cell 16 along with the carbon dioxide released from the blood is moved to one or more gas sorption devices 24 or vented. The oxygenated blood exits the photolytic cell 16 via an outlet 22 and returns to the artery of the patient.

The various particular components and/or processes of the flow through photolytic cell embodiment of the present invention are described in more detail below:

1. Transparent Substrate or Window 30

The transparent window 30 can be formed from glass, quartz slides, quartz, etc. Glass is useful in forming the transparent window provided that the UV transparency is adequate at the wavelength needed. Quartz slides are also useful because of its high UV transparency. For the transparent window, light entry into and through the transparent window can be from the back, side, or bottom. Edge illumination through the transparent window can optionally include a lens or wave guide.

The transparent window can further include a wave guide. A wave guide uniformly distributes photons (hv) from the light over the surface of the light activated catalyst. Particularly, the wave guide causes the light photons to travel in a path so that the photons maximally contact the entire layer of the light activated catalyst. Light enters the wave guide in the side of the transparent window generally parallel to the surface of the light activated catalyst that is attached to the transparent window. The wave guide allows for maximal light photon contact with the light activated catalyst without directly illuminating the side of the entire light activated catalyst attached to the transparent window. The wave guide also allows form maximal photolytic cell staking because light is not required to directly illuminate the light activated catalyst but rather can be indirectly illuminated by side or edge entry in the transparent window. The wave guide provides additional efficiency to light used in the photolytic cell because the light can be spread across the entire surface of the light activated catalyst.

2. Anode Conductor Layer 36

The anode conductor layer 36 conducts electrons formed from the reaction of water to oxygen out of the anode. The anode conductor layer prevents the electrons from reacting back with the oxygen to reform water, thereby allowing maximal formation of oxygen. The anode conductor layer is applied or attached to at least one side of the transparent window.

The anode conductor layer can be formed at least two different ways. The anode layer can be formed by attaching a thin film of uniform metallic conductor to the transparent window using vapor deposition. The film preferably has a thickness of less than about 0.2 µm. Preferably, the film is formed from gold, titanium, or indium tin oxide or other conductive material that is light transparent when thinned. Gold remains metallic at all conditions but can be very efficient at UV light blockage or reflection. Titanium can be oxidized to $TiO_2$ by adding $O_2$ to the deposition chamber to yield a possible catalyst layer with excellent adhesion.

The anode conductor layer 36 can also be formed by using photo-resist technology. Under photo-resist based technology, grids or vias are prepared with masks using vapor deposition, etching, and electroless plating. Conductor line spacing, width and thickness optimization may be required to prevent excessive attenuation, and provide sufficiently close conductor areas to sweep electrons away from the light activated catalyst layer.

3. Catalysts 32 and 34

A light activated catalyst 32 is coated onto the anode conductor layer. The light activated catalyst is photochemically activated and reacts with water to form dissolved oxygen or a free radical oxygen intermediate that is ultimately converted to dissolved oxygen. The term active oxygen (AO) in the present application defines any free radical oxygen intermediate formed in the photolytically catalyzed reaction of water that is ultimately converted to dissolved oxygen. The active oxygen formed is in the form of a peroxide, such as hydrogen peroxide, $H_2O_2$, or peroxide ion salt, hydroxyl free radical, super oxide ion, etc., and is converted into dissolved oxygen in the presence of a catalyst. The active oxygen formed depends on the light activated catalyst used. Also, depending on the light activated catalyst used, water may be photolytically converted directly into dissolved oxygen without first forming an active oxygen.

Several different catalysts can be employed for producing dissolved oxygen photochemically. One catalyst that can be used to photochemically produce oxygen is zinc oxide. By using zinc oxide, peroxide ($H_2O_2$) is produced directly from water at blood pH. $H_2O_2$ is an excellent form of active oxygen for providing sufficient potential diffusion distance, and also for the disproportionate reaction to dissolved oxygen and water via a solid $MnO_2$ catalyst (similar to green plant $O_2$ generation site) occurring photochemically at <340 nm by way of metal ion assisted disproportionation with catalase and other hydroperoxidases. Zinc oxide film has other positive attributes including, known film formation technology (e.g. via the zinc/nitrate/glycine reaction), low toxicity concerns, and low cost.

An additional catalyst that can be used to photochemically produce dissolved oxygen is tungstate ($WO_3$) that is exposed to visible light and using e-scb removal. $WO_3$ yields oxygen ($O_2$) directly from water without the need to first produce an active oxygen species. Oxygen is generated stoichiometrically and the "back reaction" is unfavored so that there is not significant competition to the direct formation of dissolved oxygen. Only visible light is needed to generate dissolved oxygen from $WO_3$, no more than about 496 nm. $WO_3$ films present low toxicity concerns. Preferably, the use of $WO_3$ further includes the removal of excess e-scb formed during oxygen formation from water.

Another catalyst suitable for reacting with water is $TiO_2$ (anatase) irradiation with, followed by dissolved oxygen production at a metal catalyst, such as a $MnO_2$ catalyst, or other similar catalyst. $TiO_2$ removes the e-scb efficiently from the production area in order to ultimately obtain good dissolved oxygen production and minimize any back reaction to reform reactants. The removal of e-scb is performed through conduction via the semi-conductor property of the $TiO_2(a)$ with enhancement via application of a small DC bias voltage. $TiO_2$ irradiation also presents low toxicity concerns. $TiO_2$ provides very high insolubility and kinetic inertness to minimize dissolution and fouling during use and maintenance. Preferably, UV light is chopped or pulsed during $TiO_2$ irradiation to allow time for the chemical reactions to occur since with continuous irradiation causes the e-scb to accumulate and force a back reaction to form water. A pause in the irradiation allows time for the slower, but still extremely fast irradiation in the range of µ sec to msec to occur.

A further catalyst for reacting with water to ultimately form dissolved oxygen is a semiconductor powder (SCP)-filled UV/VIS light transparent thermoplastic film. SCP-filled thermoplastic film is relatively inexpensive to manufacture and form into shape. SCP film is easily moldable, extrudable, cut and machined. SCP can be used very efficiently in surface applied only form. Also, SCP has low toxicity concerns. Optimized commercial products (conductive plastic filler powders) are available with good properties for dispersion, particle-to-particle electrical conductivity (for e-scb removal), and resistance to sloughing off that can be used with the present photolytic artificial lung.

The following additional preferred conditions may be used for each of the above-mentioned catalysts. First, an application of a small (e.g. up to a few volts DC) bias voltage can be applied to help ensure that the e-sch is quickly conducted away from the production site. Second, a chopped illumination, instead of a continuously applied illumination, may allow secondary chemical reactions to occur since the secondary chemical reactions are slower than the photochemical reactions and enhance photo yields by allowing the excited electrons to exit the system and not be present for regeneration of starting material, i.e., water.

Of the above-mentioned catalysts, the $TiO_2$ (anatase) catalyst followed by a second metal catalyst for disproportionation is the most preferred. When the $TiO_2$ catalyst is used, the light-titania interaction is the first step in the ultimate formation of dissolved oxygen. It is known that surface hydrated particulate $TiO_2$ (anatase) solid, $TiO_2(a)$—$OH_2$ or $TiIVO_2(a)$—OH, is an efficient UV light (hv) acceptor at wave lengths <390 nm, resulting in active oxygen formation from sorbed water and hydroxyl groups. The most probable reaction is believed to be:

$$Ti^{IV}O_{2(a)}\text{—OH} + h\nu \rightarrow Ti^{III}\text{—.OH*}$$

It is noted that other bonds to Ti have been omitted for clarity. The reactant and product of the above reaction are solid materials. In the above reaction, $H_2O$ is already bonded to the surface of the $TiO_2(a)$ catalyst as $H_2O$ or as hydroxyl ion (OH−), i.e. $TiIVO_2(a)$-$OH_2$ or $TiIVO_2(a)$-OH, respectfully. Hence, no atoms are required to move during the very fast photon absorption process. The * represents a low lying excited electronic state where the energy of the photon is used to transition or excite an electron from a nonbonding orbital on the oxygen to a molecular orbital centered on the titanium ion, hence converting the titanium into a trivalent oxidation state. The molecular orbital centered on the titanium ion is known to be a part of the semiconduction band ("scb"), and so the electron is readily conducted away from the site to form a bipolar charged grain, or, if connected to a closed DC electrical circuit, resulting in full charge separation, i.e., $$Ti^{III}\text{—.OH*} \rightarrow [Ti^{IV}\text{—.OH}]^+ + e^-_{(scb)}\uparrow$$

If the e-scb is not conducted away or otherwise removed by reaction with an oxidant present in the solution, the e-scb could react with the hydroxyl free radical and reverse or back react so that the system would return to its original state and form water. In this latter case there would be no net reaction and the photolytic energy will appear as a small amount of heat. Hence the charge separation process and removal of $e^-_{scb}$ is considered an important first step of the photolytic cell dissolved oxygen generation process.

The hydroxyl free radical (.OH) group present is used to represent the initial form of the active oxygen generated by the photolytic process. It is not certain that .OH is the dominant species present when $TiO_2(a)$ is photolyzed. The active oxygen formed could generally be in the form of a superoxide, hydrogen peroxide, or a hydroxyl free radical. However, the form of this active oxygen produced has sufficient thermodynamic driving force to form active oxygen from water. For the $TiO_2(a)$ catalyst at neutral pH, these highly reactive hydroxyl free radicals either back react as described above, or rapidly dimerize to form (μ-peroxo) titanium (IV) and hydrogen ions, i.e.

$$2Ti^{IV}\text{—.OH} \xrightarrow{\text{Fast}} Ti^{IV}\text{—O—O—}Ti^{IV} + 2H^+$$

These H+ ions are valuable for blood-$CO_2$ level control. The rate of dissolved oxygen production is the rate at which the active oxygen splits out to form $O_2(aq)$ and reforms $TiO_2$ (a), i.e.

$$Ti^{IV}\text{—O—O—}Ti^{IV} \rightarrow Ti^{IV}\text{—O—}Ti^{IV} + \tfrac{1}{2}O_{2(aq)} \text{ (as dissolved oxygen)}$$

In an unwanted but unharmful second side reaction, any $O_2(aq)$ produced can react with e-scb previously produced but not yet conducted away. These e-scb negative charges tend to reside on the surfaces of the $TiO_2$ particles so that the negative charge are most separated. Therefore, these e-scb electrons are available for reduction reactions with $O_2$ or the μ-peroxide linkage to produce species such as $O_2$—, $O$=, $O$—, etc., thereby decreasing dissolved oxygen yields. In order to minimize side reaction, the illumination is pulsed instead of continuous. The delay caused by illumination pulsation allows the e-scb to be conducted away in one direction and the dissolved oxygen to diffuse away in another (E. Pelizzetti, M. Barbeni, E. Pramauro, W. Erbs, E. Borgarello, M. A. Jamieson, and N. Serpone, Quimica Nova (Brazil), 288 (1985)). Also, illumination pulsation prevents the local populations of $O_2(aq)$ and e-scb from becoming so high that reaction between them becomes fast. The pulse rates involved are extremely short in the μsec-msec range so that there is little effect on $O_2(aq)$ production rates. Enhanced yields are also possible for photolytically established charge separation when a bias voltage is present across the coating. (X. Z. Li, H. L. Liu, and P. T. Yue, Envison-Sci-Technology, 2000, 34, 4401-4406.) A small bias voltage may also be used to further reduce the amount of e-scb present and produce more dissolved oxygen.

Another way to increase the amount of dissolved oxygen production in the $TiO_2(a)$ system is to provide a means to speed the rate of release of the trapped μ-peroxide as hydrogen peroxide as to active oxygen.

$$Ti^{IV}\text{—O—O—}Ti^{IV} + H_2O \rightarrow Ti^{IV}\text{—O—}Ti^{IV} + H_2O_{2(aq)}$$

$H_2O_2$ is an excellent form for the active oxygen species as it readily migrates and is easily catalyzed to disproportionate into dissolved oxygen and water.

$$2H_2O_{2(aq)} \xrightarrow[\text{fast}]{\text{Catalyst}} O_{2(aq)} + 2H_2O$$

Stable free radicals (SFRs) can be used to release the trapped @-peroxide as hydrogen peroxide. SFRs can exist as free radicals for extended periods of time relative to the hydroxyl free radical. SFRs have been found useful for promoting electron transfer reactions. They electronically and reversibly rearrange into reduced or oxidized species one electron at a time as set by the reaction conditions. Biological systems are known to use SFRs as respiratory carriers, such as quinone coenzymes including ubiquinone, vitamin K, etc. The SFR shuttles the reactivity from the point of generation to the point of $H_2O_2$ production, or even directly to the metal ion $MnO_2$ catalyst for dissolved oxygen production. Components found in biological systems such as vitamins E, C, K, etc. also may function in the role of SFRs except without recycle. At least four classes of SFRs exist from which a suitable agent can be selected: hindered hydroxylated aromatics (quinones, substituted phenolics); organic peroxide precursors (alcohols, etc.); peracid precursors (acylating agents, etc.); and nitroxides, RN→O.

Therefore, for the $TiO_2(a)$ photocatalyst to be useful, a means for releasing the μ-peroxide energy is needed, such as soluble $H_2O_2$, since $H_2O_2$ can diffuse to the $MnO_2$ for dissolved oxygen production, or by conducting the oxidizing power to another active oxygen form, such as SFRs in the adjacent solution that can be used in dissolved oxygen production, or using the TiIV—O—O—TiIV content to electronically remove electrons from the $MnO_2$ cluster/particle (as is done in green plant photosynthesis by the "D" protein). In the last means, only an electron flows from the water through the $MnO_2$ to the μ-peroxo linkage through delocalized bonds. This electron replaces the e-lost from the $TiO_2$(a)-OH system as e-scb.

The formation of $H_2O_2$ as the active oxygen is valuable since $H_2O_2$ can be rapidly converted to dissolved oxygen in 100% yield using many different methods: thermally; metal ion catalysis; particulate/surface catalysis; base catalysis; and free radical reaction with reductant initiation. Preferably, metal ion catalysis, such as, $MnO_2(s)$, provides an efficient catalyst for $H_2O_2$ disproportionation to water and $O_2$, on thin film substrate constructs.

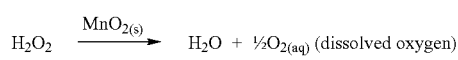

Photo catalyst systems such as zinc oxide, ZnO, release peroxide as the active oxygen more readily than does $TiO_2$. Less acidic metal ions under the Lewis acid/base theory definition cannot sufficiently stabilize the highly alkaline peroxide ion relative to water protonation (pKa1 of $H_2O_2$ is 11.38 (25° C.)) to form it within the solid phase, and so hydrogen peroxide, $H_2O_2$, is readily formed from ZnO:

ZnO films and particles can be prepared in a number of ways with varying but controlled composition, morphology and porosity. For example, mirrors of zinc, doped zinc, and zinc alloys and can be sputtered down onto an optically transparent support, followed by oxidation with $O_2(g)$. This treatment produces a metal/metal oxide (Zn/ZnO) film. Another highly effective approach to semiconducting ZnO-based films is to utilize a process for optical glass coatings. (L. R. Pederson, L. A. Chick, and G. J. Exarhos, U.S. Pat. No. 4,880,772 (1989).) The optical glass coating technique is based on applying a zinc nitrate/glycine aqueous solution as a dip or spray, followed by drying (110° C. for 15 min), then heating (450-500° C. for 3 min) to initiate a self-oxidation reaction during which the carbon and nitrogen exits as gases leaving an adherent yet porous film bonded to the underlying surface (e.g. glass) and is referred to as the glycine nitrate process. (L. R. Pederson, L. A. Chick, and G. J. Exarhos, U.S. Pat. No. 4,880,772 (1989).) The ZnO film is normally produced doped with alumina by including aluminum nitrate in the aqueous formulation for the initial dip. Many other metal ion blends are also possible with this technique.

Tungstate only requires visible light to produce dissolved oxygen, and produces dissolved oxygen directly without requiring a second catalyst to form dissolved oxygen. The lower photon energy requirement for $WO_3$ is due to the smaller band gap of 2.5 eV versus at least 3 eV for $TiO_2$(a). As with the $TiO_2$ anatase system, high yields are possible with the $WO_3$ catalyst if the e-scb is removed. The production of $O_2$ increases very significantly if $RuO_2$ (ruthenium oxide) is placed on the surface of the $WO_3$. This is consistent with the fact that $RuO_2$ is a known good catalyst for $O_2$ production and so represents a route to improving other approaches.

An advantage may exist if the dissolved oxygen producing film could be a filled plastic. Such materials are often inexpensive and manufactured easily. Commercial sources exist for semi-conducting, low light absorbing, inorganic fillers for plastics which are supplied in ready made condition for incorporation into plastics, making the plastics electrically conductive. For example, E.I. DuPont Nemours, Inc. sells electroconductive powders (EPC) under the trade name ZELEC® ECP for such purposes. The conductive substance in ZELEC® ECP is antimony-doped tin oxide ($SnO_2$:Sb). The bulk of these materials, onto which the conductor is coated, are familiar inorganics such as mica flakes, $TiO_2$, and hollow silica shells, or ECP-M, ECP-T and ECP-S respectively. Pure $SnO_2$:Sb-based material is designated ECP-XC and is a much smaller particle than the other materials. About 25-45% by weight of the ECP products are used so that the particles are sufficiently close to each other to provide internal electrical connections throughout the otherwise non-conducting plastic. ECP-S and ECP-M normally perform best for lower concentrations. Thin films of ECP-XC can provide an attractive coating because they are very fine grained and strongly light absorbing.

The $TiO_2$ layer can be formed a variety of ways. The $TiO_2$ layer can be formed by sol gel, drying and baking. A product under the trademark LIQUICOAT® from Merck & Co., Inc., which hydrolyzes Ti(OR)4 type material in water to form $TiO_2$ and 4ROH can be used to form the $TiO_2$ layer under a sol gel/drying/baking process. $TiO_2$ can also be formed from preparing an anatase suspension from dry powder, then dipping, drying, and baking the suspension to form the $TiO_2$ layer. Another way the $TiO_2$ layer can be formed is by e-beam evaporating titanium and subsequently exposing the titanium to $O_2$ within a deposition chamber. The $TiO_2$ layer can also be formed by adding titanium salt to water and adjusting the pH to ~2-7 to form a suspension, then dipping the suspension and allowing the suspension to dry.

Active oxygen is created from $TiO_2$ by irradiation with UV light, but the chemical form of the active oxygen is very reactive and can be lost by side reaction occurring in close proximity to the $TiO_2$ particle surface where active oxygen is generated. There are at least three ways to minimize the loss of active oxygen to unwanted side reaction: 1) move the active oxygen to dissolved oxygen conversion point closer to the active oxygen generation point, i.e. move the metal ion catalyst as close as possible to the $TiO_2$, which may require intimate contact between these two materials, in the order of angstroms; 2) electrically connect the two points, as is done in photosynthesis by a protein capable of conducting electrons; or 3) convert the active oxygen into a longer lived intermediate active oxygen species that has time to migrate to more distant $MnO_2$ centers for conversion to dissolved oxygen.

The amount of active oxygen lost by side reactions can be minimized by introducing an active oxygen carrier molecule into the media, or "D," by analogy to a photosynthetic system. Agents for use with species D can be selected from two groups, those that readily form organic peroxides, and those that form "stable" (i.e. long-lived) free radicals. Organic peroxides are useful because they easily produce dissolved oxygen when contacting $MnO_2$, and readily form by oxygen insertion. The organic peroxide reactions are as follows:

$$[TiO_2]—Ti^{IV}—OH+h\nu->\{[TiO_2]—Ti^{III}.OH\}$$

where the excited electronic state corresponds to the ligand-to-metal charge transfer (free radical pair), and is followed by the reaction:

$$\{[TiO_2]—Ti^{III}.OH\}+H_2O->[TiO_2]—Ti^{IV}—OH+H^+\\.OH$$

where conduction of the e– into the semiconductor conduction band and away from the side of the particle near the .OH prevents recombination of that e–. As shown in the reaction above, the $TiO_2$ anatase is regenerated. The above reaction produces a hydrogen ion for eventual $CO_2$ removal. Also, the active oxygen produced in the above reaction is in close proximity to $TiO_2$ as a free radical hydroxyl groups, .OH.

As .OH is extremely reactive, lasts only for a very short time and does not diffuse far. One way to increase the amount of time that .OH is present is by introducing a species that stabilizes the .OH. Similar to photosynthesis, a species "D" is introduced into the test system to capture the hydroxyl free radical in a longer lived species. The species D is generally shown the in following chemical reaction:

$$D+.OH->D^*$$

where D can be RC(O)OH:

$$RC(O)OH + \cdot OH \longrightarrow RC(=O)OOH + \cdot H$$
$$\text{organic peracid}$$

or D can be $R_3COH$:

$$R_3COH + \cdot OH \longrightarrow R_3COOH + \cdot H$$
$$\text{Alcohol} \quad\quad\quad\quad \text{organic peroxide}$$

or D can be a free radical scavenger that forms a stable free radical:

$$R—N=O + \cdot OH \longrightarrow [R—N=O]^{\cdot *} + OH^-$$
$$\text{free radical} \quad\quad\quad\quad \text{stable}$$
$$\text{scavenger} \quad\quad\quad\quad \text{free radical}$$

or D can be 2,6-di-tertbutyl phenol:

$$t\text{-Bu-Ar}—OH+.OH->t\text{-Bu-Ar}—O^*+H2O$$

The 2,6-di-tertbutyl phenol is the most desired D species, as a strongly reducing .H radical is not formed that would consume OH— and $[TiO_2]$—TiIII in wasteful reactions, regenerate the starting materials, and result in a low photochemical yield.

The catalyst used to convert active oxygen into dissolved oxygen includes metal ions capable of redox cycling, such as FeII, FeIII, CuI, CuII, CoII, CoIII, MnII, MnIII, MnIV, etc., or metal oxides formed from metal ions capable of redox cycling, such as manganese dioxide, $MnO_2$. The present reaction produces dissolved oxygen directly from water and by-passes the gaseous state. The $MnO_2$ catalyst is most preferred because it forms dissolved oxygen efficiently and is not highly selective of the active oxygen form.

One way to facilitate the conversion of active oxygen to $O_2$ is by doping the surface of the $TiO_2$ anatase with manganese (Mn). Surface doping the $TiO_2$ with Mn provides a highly productive active oxygen to $O_2$ conversion catalyst. Active oxygen disproportionation is rapid when dropped on a Mn-doped anatase. Alternatively, active oxygen can also be converted to $O_2$ by placing $MnO_2$ on the surface of the anatase in conductive form. In this form, electrons are catalytically passed from water to the active oxygen region of the anatase. Such an arrangement more closely mimics photosynthesis $O_2$ production.

Another way to convert active oxygen to $O_2$ in the photolytic cell is by using a $MnO_2$ octahedral molecular sieve (MOMS) material as the dissolved oxygen catalyst. The MOMS material has an open gel-like structure and is closely related to zeolites in structure. The MOMS material is easily formed from manganese salts through precipitation and drying.

Active oxygen may also be converted to $O_2$ in the photolytic cell by a superoxide dismutase (SOD) catalyst. SOD catalyst is already available in the human body and can provide the required conversion of active oxygen, e.g. as $O_2$—, into a dissolved oxygen precursor, i.e. $H_2O_2$, to supplement the photolytic cell and Mn-doped anatase.

Blood is routinely exposed to active oxygen forms and blood already has built-in measures for self protection against low levels of excessive active oxygen. ("Inorganic Biochemistry", G. L. Eichhorn (Ed)., Chap. 28, p 988 (Elsevier, Scientific Publ., NY (1975), and "Advances in Inorganic and Bioinorganic Mechanisms", A. G. Skes (Ed), p 128 (1986) (Academy Press, NY)) Active oxygen forms within the body in the form of species such as peroxides (R—O—O—H) and superoxide ($O_2$-(aq)), which are disproportionated to dissolved oxygen and $H_2O$ respectively by hydroperoxidases, such as catalase which contains zinc ion, peroxidase which contains iron ion, etc., and superoxide dismutase metal ion-based enzymes, such as ferriprotophyrin IX. Alternatively, these enzymes can utilize active oxygen forms to oxidize a wide range of chemical reductants such as ascorbic acid and other vitamins such as such as vitamin E and vitamin K. Although the photolytic artificial lung does not rely on such protection mechanisms, it is noteworthy that low levels of such molecules are not new to body chemistry and that conventional mechanisms for handling such exposures exists.

4. Blood Exchange

Hemoglobin from blood follows the following steps of reactions within the photolytic cell.

$Hb(h.s. Fe^{II})+O_2 \delta Hb(l.s. Fe^{II})O_2$
$HbO_2+2H^+(pH\ 6.8\text{-}7.6)\delta H_2Hb2^++O_2$
N— of two alpha-chains (pKa ι 8.0) and His β146
(pKa ι 6.5) residues are bases for $H^+$ reaction
$CO_2+H_2O\ \lambda H_2CO_3\ \lambda H^++HCO_3^-$
$Hb(R—NH_2)+CO_2\ \lambda R—NH—COO^-+H^+$ When water reacts with a light activated catalyst, the hydrogen ion that is released rapidly reacts with an HCO3-ion and forms H2CO3. The photolytic cell has excess $HCO_3$— ions to react with hydrogen ions.

The photolytic cell allows the blood to achieve the proper mass balance. The mass balance of blood traveling through the photolytic cell is as follows:

$$Hb(RNHCOO^-) + 2H^+ \rightleftharpoons HbNH_3^+ + CO_2$$

-continued $$HCO_3^- + H^+ \rightleftharpoons H_2CO_3 \xrightarrow{CA} H_2O + CO_2$$

$$HbNH_3^+ + O_2 \rightleftharpoons Hb \cdot O_2 + 2H^+$$

$$2H_2O + h\nu \rightleftharpoons O_2 + 4H^+ + 4e^-$$

$$H^+ 4e^{-+} + 2 \text{ quinone} \rightleftharpoons 2 \text{ hydroquinone}$$
$$\quad\quad\quad\quad\quad\quad Q \quad\quad\quad\quad\quad\quad H_2Q$$

Net Reaction: $Hb(RNHCOO^-)+HCO_3^-+H^++H_2O+h\nu+2Q \approx 2\ CO_2+Hb.O_2+2H_2Q$.

Alternatively, quinone can be replaced with $Fe(CN)_6^{3-}$. The quinone or Fe(CN)63-Q could be in homogeneous solution or film form.

5. Cation Exchange Membrane 46

The cation exchange membrane 46 allows for the diffusion of cations in the photolytic cell. Particularly, the cation exchange membrane allows a cation, such as a sodium ion (Na+) from blood to diffuse through the membrane and subsequently form sodium hydroxide (NaOH) in the catholyte. The cation exchange membrane is commercially available under the trademark NAFION® and is available from E.I. DuPont Nemours Inc. NAFION® cation exchange membranes are a perfluorosulfonic acid/PTFE copolymer in an acidic form. Although NAFION® cation exchange membranes are the preferred membrane, one skilled in the art would recognize that other cation exchange membranes are also suitable in the photolytic cell.

The anodic compartment of the photolytic cell has the following series of reactions:

$$h\nu + 2H_2O \xrightarrow{TiO_2} \text{"AO"} + 2H^+ + 2e^-$$

$$AO \xrightarrow{MnO_2} \tfrac{1}{2}O_2 + H_2O$$

$$2H^+ + 2HCO_3^- \longrightarrow 2H_2CO_3$$

$$2H_2CO_3 \xrightarrow{CA\ cat.} 2H_2O + 2CO_2$$
& uncat.

$$2CO_2 \longrightarrow 2CO_{2(g)}$$

$$\tfrac{1}{4}Hb + \tfrac{1}{2}O_2 \rightleftharpoons \tfrac{1}{2}Hb{:}O_2$$

The overall net anodic reaction from the above reactions is as follows:

$$h\nu + \tfrac{1}{4}Hb + 2NaHCO_3 \rightarrow 2CO_{2(g)}\mu + H_2O + \tfrac{1}{2}Hb_{0.5}O_2 + 2e^- + 2Na^+$$

The two electrons formed in the anodic reaction are conducted away to the cathode via the anode conductor layer. The two Na+ ions are moved to a catholyte via a cation exchange membrane.

6. Catholyte 48

Sodium hydroxide (NaOH) builds in the catholyte during the series of reactions in the photolytic cell. It is preferred that the NaOH is purged occasionally from the catholyte. If sodium chloride (NaCl) is used in the catholyte instead of NaOH, NaCl(s) may eventually form within the catholyte and would periodically be purged.

The reactions occurring in the cathode of the photolytic cell are as follows:

$$2NaHCO_3 \lambda 2Na^+ + 2HCO_3^-$$

$$2e^- + 2H_2O + \approx H_{2(g)} + 2\ OH^-$$

$$2\ OH^- + 2HCO_3^- \approx 2\ CO_3^= + 2H_2O$$

$$4Na^+ + 2CO_3^{2-} \lambda 2Na_2CO_3$$

The overall net cathodic reaction is as follows:

$$2e^- + 2Na^+ + 2NaHCO_3 \rightarrow H_{2(g)}\mu + 2Na_2CO_3$$

The Na2CO3 that is produced causes pH to rise. Based upon the overall anodic and cathodic cell reactions, the overall net photolytic cell reaction is:

$$h\nu + \tfrac{1}{4}Hb + 4NaHCO_3 \rightarrow H_{2(g)} + 2Na_2CO_3 + 2CO_{2(g)} + H_2O + \tfrac{1}{2}Hb_{0.5}O$$

7. Battery/Current Regulator

As shown in FIG. 4, the photolytic cell can include a battery 49, current regulator 50, or resistor 52. An electrical current formed from a battery 49 allows electrons to flow from the anode 36 to the cathode 38. The initial bias voltage caused by the current supplied from the battery initiates the removal of electrons formed during the conversion of water to dissolved oxygen and prevents the electrons from reacting with the active or dissolved oxygen to reform water. The initial bias voltage also allows more dissolved oxygen to be produced as the removal of the electrons minimizes the reformation of water. Additional external electrical contacts can monitor or apply a particular voltage to the photolytic cell.

The current regulator and resistor help control the flow of electrons from the anode to cathode, thereby controlling the amount of dissolved oxygen formation. The resistor creates a fixed control in the current flow, whereas the current regulator can be adjusted to increase or decrease the resistance of the current flow. Increasing the resistance of the current lowers the number of electrons flowing from the anode to the cathode, thereby lowering the overall production of dissolved oxygen. Decreasing the resistance of the current increases the flow of electrons from the anode to the cathode, thereby increasing the amount of dissolved oxygen produced.

8. Optimal Gas Sorption Device 24

Continual venting of carbon dioxide gas out of the photolytic cell presents the problem of potential infection. A gas sorption device minimizes and provides control over potential infection risks by avoiding continuous venting of the $CO_2$ to the atmosphere. The gas sorption device captures $CO_2$ gas released from the oxygenated blood in a concentrated form. The concentrate can be processed or disposed of occasionally so that the sterility of the photolytic cell is not continuously subjected to possible contaminants due to the continual venting of the $CO_2$ gas.

$CO_2$ can be captured using a number of different ways by a gas sorption device 24. The gas sorption device can use the process of chemi-absorption and convert $CO_2$ into a concentrated solid or solution form. The concentrate formed in the gas sorption device can then be disposed of as disposable cartridges having liquid or solid $CO_2$, or regenerated.

9. Light Supply 20

The light supply is used in the photolytic cell to provide the photon energy necessary to activate the catalyst converting water into oxygen. The light source can be from any known light source including, but not limited to, sunlight, UV light, laser light, incandescent light, etc., depending on the activation requirement for the light activated catalyst used. Preferably, the blood flowing through the photolytic artificial lung is not exposed to the light in order to prevent irradiation of the blood.

The light source may provide a particular wavelength of light depending upon the catalyst used. When tungstate ($WO_3$) is used as a light activated catalyst, the light source exposes visible light in order to activate $WO_3$. When $TiO_2$ or ZnO is used as a light activated catalyst, the light source used has a wavelength in the UV range.

Preferably, the light source used in the photolytic artificial lung is a laser light. The wavelength of laser light can be manipulated in order to attain a higher efficiency in exciting the light activated catalyst and forming active oxygen. Also, laser light allows the photolytic artificial lung to dissipate less overall heat. The laser light can be directed in a small area to energize the light activated catalyst and avoid contact or irradiation with other components of the photolytic artificial lung. A particularly preferred laser light that can be used to activate $TiO_2$ is an argon laser at 364 nm (400 mwatts/cm2), which has a total power of about 2 watts, although other UV sources, including an HG arc lamp at 365 nm line, are also available.

It is preferred that the light from the light source be evenly spread within the photolytic cell. The even spreading of the light from the light source allows for maximal excitation of the catalyst in order to convert more water into either active oxygen or dissolved oxygen. Along these lines, light from the light source can enter the photolytic cell through the transparent window from many positions. Light from the light source can enter directly through the transparent window and come into contact with the catalyst. Alternatively, light can enter the transparent window from a side, back, bottom, or corner position and move through the transparent window by a wave guide to provide photon energy and excite the light activated catalyst. Side entry of light into the transparent window of the photolytic cell occurs at about at least a 68° angle. Preferably, side entry of light into the transparent window occurs at an angle of from about 70° to about 80°.

10. Pump

A peristaltic pump or some other simple pump drives blood through the photolytic artificial lung. The pump draws venous deoxygenated blood from a patient and moves the blood through the photolytic artificial lung. Preferably, the photolytic artificial lung only requires a pump to draw blood from a patient, as the flow produced by the pump drawing blood from the patient also moves the blood through the photolytic cell for oxygenation and back into the patient.

11. Sensors Monitoring Reaction Chemistry

The photolytic artificial lung can include one or more sensors that monitor the different chemical reactions occurring within the photolytic cell. The sensors can be used to measure for potential toxins and toxin levels. Various sensors and sensor systems can be used including visual observations of color changes of redox indicator dyes or gas bubble formation, closed electrical current measurements and pH measurements, and dissolved oxygen probe analysis. Gas chromatography assays can also be performed. A dissolved oxygen probe can be used to test and monitor $O_2$ generation, as dissolved oxygen, in real time. Also, the photolytic artificial lung can incorporate one or more portals to insert a dissolved oxygen probe, $CO_2$ probe, pH monitor, etc. in different locations if necessary. The photolytic artificial lung can also incorporate separate sampling chambers to trap gas bubbles for testing. These sampling chambers could also incorporate a device, such as a septum for a hypodermic needle for instance, to obtain a sample for further testing. One skilled in the art would recognize numerous sensors could be used for monitoring the reaction chemistries occurring within the photolytic cell.

The photolytic device and photolytic cell can also include one or more process regulator devices that respond to the readings provided by the sensors. The process regulator devices increase or decrease the amount of dissolved oxygen or $CO_2$ output, lower toxin levels, etc., depending on the requirements of the patient or of the photolytic cell. It is within the purview of one utilizing the photolytic artificial lung to determine what process regulator devices are required.

All of the seals in the photolytic artificial lung are made of an inert material that properly seals blood flowing through the photolytic artificial lung from accidental contamination. The seals of the photolytic lung should also be formed of a material that does not interact with the blood. Preferably, the seals are formed of a silicone-based material.

Laminar flow is minimized within the photolytic artificial lung. Minimization of laminar flow is accomplished by using current commercial cells, such as electrodialysis, electrodeionization, etc. Commercially available cells accommodate electrodes, membranes, and thin liquid chambers with flow distributors, and provide good seals and corrosion resistance. The cells are available in lab scale units for process development work. A particularly preferred commercial cell is the FM01-LC device from ICI Chemicals and Polymers, Electrochemical Technology, Cheshire, UK.

Multiple Photolytic Cells

Preferably, the photolytic artificial lung uses a plurality of photolytic cells in a stacked formation. The plurality of photolytic cells receives blood flow from the venous circulation and is exposed to photo-activation via a directed laser light source. The stacking of a plurality of photolytic cells allows for a large overall surface area for blood to receive maximal exposure to dissolved oxygen. Also, stacking a plurality of photolytic cells allows the overall photolytic artificial lung to achieve a smaller size, thereby allowing the photolytic artificial lung to be miniaturized.

Moreover, it has been found that one is able to control material properties of the photolytic surface, resulting in an expression of the maximal rate by which dissolved oxygen is increased (or carbon dioxide decreased) as a function of reaction surface area and laser power. If desired one can use the materials described herein to create a photolytic chamber, which incorporates optimal reaction kinetics and fluid mechanical modeling of blood flow in relation to the photolytic surface. The selected materials can be used in selecting the boundary conditions for the full chamber, emulating the fundamental relationship between the alveolar surface and the pulmonary capillary.

The following examples are for the purposes of further illustrating photoactive layers for whole blood oxygenation in accordance with the present disclosure. The examples are merely illustrative and are not intended to limit photoactive layers in accordance with the disclosure to the materials, conditions, or process parameters set forth therein. All parts are percentages by volume unless otherwise indicated.

EXAMPLES

Example 1

This example illustrates the fabrication of photoactive layers. Oxide materials were added to a substrate using a spin coating technique. Glass slides containing the conducting layer were placed on a vacuum. For the $TiO_2$ coating, 0.5 g of the acid treated material was added to 40 ml isopropanol and mixed for 30 minutes. 0.050 ml $H_2O$ and 0.100 ml titanium (IV) tetra(isopropoxide) (TTIP), a sol-gel reagent, was added to this solution. After mixing for 30 minutes, the solution was added drop-wise to the rotating substrate for a total volume of about 12 ml. In the case of the constructs containing $MnO_2$, following the addition of 9 ml of $TiO_2$ slurry, 0.20 g $MnO_2$ was added to the remaining slurry. Exactly four ml of the resulting solution was then added drop-wise to the substrate at spin coating conditions. As a modification of this technique, $RuO_2$/Pt doped $TiO_2$ (0.125 g) was added to 10 ml isopropanol. After 15 minutes of mixing, 50 uL water and 25 uL TTIP was added and allowed to mix for an additional 15 minutes. The solution was then added drop-wise to the substrate for a total volume of 9 ml. The sol-gel coated samples were all allowed to air dry at room temperature overnight. They were then placed in a preheated tube furnace and heated for 45 minutes at elevated temperature under a 1 L/min. flow of nitrogen. Samples containing conducting layers of Ti or indium tin oxide were heated at 350° C., while samples containing Ni or Cr (metallic conducting films) were heated at 209° C.

Example 2

In addition to batch cells, a flow-through test cell was constructed to associate flowing liquids (such as blood) with photolytic output. A modified FM01-LC Electrolyser, operating in a divided cell mode with a Nafion™ cation exchange membrane was used. The anode was optically transparent, and illumination was achieved side-on by UV light (354 nm) using a filter and UVA fiber optic lamp source. The catholyte was Locke's-Ring solution, and the anolyte fresh whole bovine blood containing anticoagulant. The photolytic surface was $TiO_2$ on a quartz plate. Fluids were maintained at 37° C. using an in-line heat exchange jacket, and flow was 80 cc/min by a peristaltic pump. The flow-through cell consisted of a 3 ml photolytic chamber, with a single active surface of vacuum deposited Ti metal, a coating of $TiO_2$ (anatase) and optionally a $MnO_2$ layer. These films were prepared as described above for the batch test films, except on larger glass and quartz substrates (effective area ~5 in2). The uncoated glass/quartz side of the plates was illuminated by filtered UV light.

Data collected were pH, electrical current, dissolved oxygen (DO), $pO_2$, $pCO_2$, $SO_2$, and oxyhemoglobin as a function of laser irradiation and the presence or absence of bias voltage.

Example 3

This example illustrates real-time measurement of dissolved oxygen (DO): A liquid phase in line reaction chamber was used to monitor dissolved oxygen production. This device utilized a Clark Electrode to measure dissolved oxygen (DO). A two-point calibration procedure was used to calibrate the dissolved oxygen sensor. Dasse K A, Monzyk B F, Burckle E C, Busch J R, Gilbert R J., *Development of a photolytic artificial lung: Preliminary concept validation, ASAIO Journal*, 48:556-563, 2003. A low bias voltage was applied to the cell through a DC power source, sufficient to insure proper anode-to-cathode electron flow direction, to promote immediate removal of photo-generated electrons, but insufficient to drive electrochemical side reactions, as evidenced by the lack of current flow in the absence of illumination. Dasse K A, Monzyk B F, Burckle E C, Busch J R, Gilbert R J., *Development of a photolytic artificial lung: Preliminary concept validation, in press, ASAIO Journal*, 2003. Electrical current was measured with a high-impedance VOM multimeter. The light was directed to the reaction chamber through a liquid light pipe, and filtered to produce light of only 365 nm; the intensity at this wavelength was 88.1 mW/cm2 at the exit point of the light pipe. It would be preferred to make measurements to record actual photon flux impinging on the photolytic surface as substantial light losses occur at this interface. Heating of the solution during illumination was prevented by use of a light filter at the 365 nm wavelength light that is efficiently absorbed by the anatase film. A water-jacketed surrounding the reaction chamber was used to maintain a physiologically significant and constant 36° C. throughout the experiments.

Example 4

This example illustrates the measurement of blood gas parameters. Conventional blood gas analyses were made using a blood gas analyzer. Precise volumes of blood samples (~0.25 ml) were withdrawn at specific times by needle fitted syringe from an in-line septum access port and analyzed using the NPT7 Blood-Gas Analyzer (Radiometer, Inc). This instrument gives readout of concentration measurements of total hemoglobin, oxyhemoglobin, deoxyhemoglobin, methemoglobin, partial pressure of $O_2$, partial pressure of $CO_2$, $SO_2$, and pH. As described above, a Clark electrode was also used to monitor for total dissolved oxygen (DO) in real time, thus comprising an independent verification and measurement of this key parameter.

Figure 2:
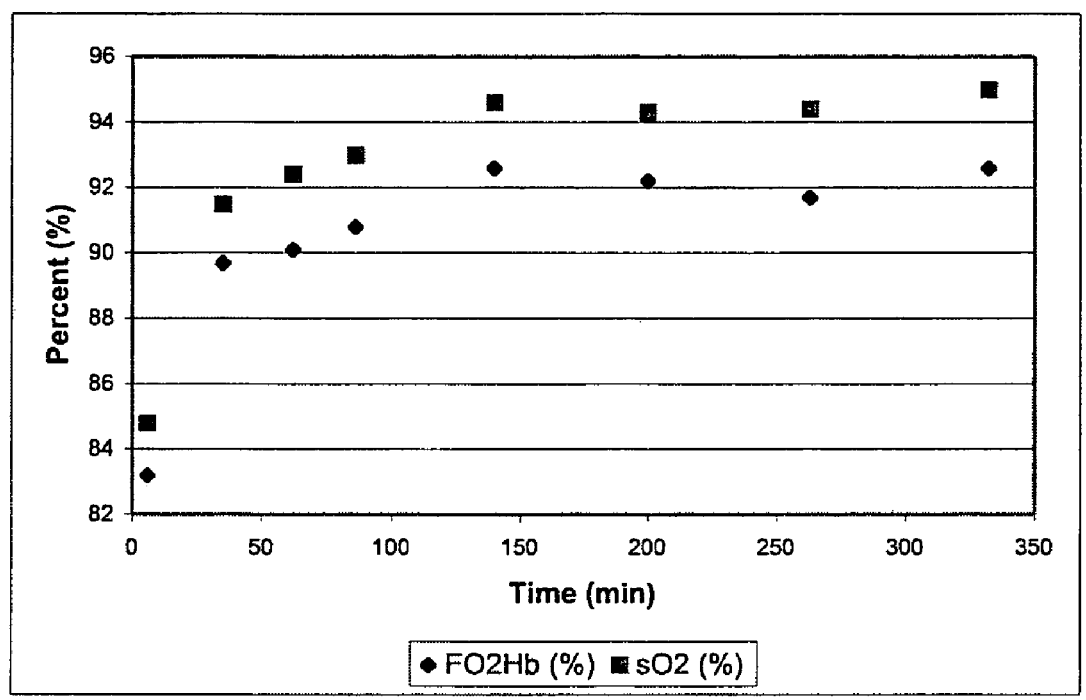
FIG. 2 is a graph showing photolytic generation of dissolved oxygen and enhanced oxyhemoglobin in whole blood. The vertical scale is in percent of the measured amount and the horizontal scale is time in minutes. A modified FM01-LC Electrolyser, operating in a divided cell mode using a NAFION™ membrane was used to separate catholyte and anolyte solution. The anode was optically transparent, and illumination was achieved side-on by UV light (354 nm) using a filter and UVA fiber optic lamp source. The catholyte was Locke's-Ringer solution, and the anolyte was anticoagulated, fresh whole blood at 37° C. using an in-line jacket. Flow was regulated by a peristaltic pump at 80 cc/min. Oxyhemoglobin, (represented in the figure as $FO_2Hb$) rapidly increased with laser illumination from 83% to 92% and remained stable throughout the trial. The term $FO_2Hb$ indicates the percent of hemoglobin, which contains bound oxygen, i.e. hemoglobin saturation. The term $sO_2$ indicates the extent to which dissolved oxygen is contained in the water phase of blood; in effect the degree to which dissolved oxygen may be contained in water before it separates out as $O_2$.

Filtered UV illumination of the metal oxide light-absorbing surface opposite the blood in the flow-through cell described above resulted in near complete oxygen saturation of the blood circulating on the opposite side of the photolyzed surface (see FIG. 2). The fraction of oxyhemoglobin (represented in the FIG. 2 as $FO_2Hb$) rapidly increased from 83% to 92% and remained stable throughout the trial period. The extent to which dissolved oxygen is dissolved in the serum phase of the blood, represented as a percentage, is depicted by the term $SO_2$, or "soluble $O_2$." by the blood gas instrument. $SO_2$ is that portion of the total $O_2$ resident in the blood that is normally supplied through the alveolar membrane/pulmonary capillary wall interface, and is equal to 100*(DO/DOmax), where DO is the amount of dissolved oxygen, and DOmax is the maximum solubility of $O_2$ in blood serum at the temperature of the blood, a reference value automatically calculated from an algorithm pre-programmed into the blood gas analyzer. This is the percent of maximum $O_2$ that is ready to diffuse into red blood cells and bind to hemoglobin. $SO_2$ also predicts when $O_2$ gas bubbles can form due to supersaturation, i.e. when dissolved oxygen reaches levels such that $SO_2 \geq 1.0$. Such bubbles would be 100% $O_2$, saturated with humidity, and so would re-dissolve quickly and completely by the tissue as the demand for $O_2$ by the tissue consumes it and if production of dissolved oxygen is slowed. Hence excessive dissolved oxygen production is easily controlled in the envisioned process. The fact that the $FO_2Hb$ and $SO_2$ curves varied in a parallel manner (see FIG. 2) confirm the $O_2$ generation results, and demonstrates that near complete oxygenation of hemoglobin content of the blood was achieved. It also replicates previous results 18 in a complex matrix, that of whole blood.

The effect of UV light illumination on pH, the partial pressures of $CO_2$ and $CO_2$, oxygen saturation in the blood serum, fraction of hemoglobin saturated with oxygen, and the percent of blood methemoglobin were determined at various time points, from 16 to 460 minutes, in a recirculating flow loop (Table 1). Significantly, blood pH and the partial pressures of $O_2$ and $CO_2$ stabilized at approximately 60 minutes, and remained so for the duration of the experiment. It should be noted that the pH of the anolyte dropped only during the initial formation of oxyhemoglobin, which can be understood using conventional blood chemistry coupled with the previously described photochemistry 18 by the following reaction:

$$2H_2O + Hb + h\nu(light) \rightarrow O_2Hb + 4H^+ + 4e^-$$

These electrons provide the basis for the observed electrical current, and the H+ ions caused the observed small drop in pH. The drop in pH is small as most of the H+ ion are immediately consumed through $CO_2$ formation from the bloods' bicarbonate buffer, as follows:

$$HCO_3^- + H^+ \rightarrow H_2CO_3 \xrightarrow{\text{carbonic anhydrase}} H_2O + CO_2$$

resulting in the stabilization of blood pH and enables the release of $CO_2$ from the blood, the second major requirement for complete blood gas control by the lung. The percent dissolved oxygen of saturation in the water phase of the blood ($SO_2$) and oxyhemoglobin ($FO_2Hb$) increased in parallel in the flowing blood with continuous laser illumination of the photoactive surface, reaching maximum values at 58 minutes, then remaining stable to the end of the trial. It was additionally considered that the exposure of the $TiO_2$ surface to continuous UV light (even without direct exposure of the blood) could have toxic oxidant effects, resulting in an increased percent of hemoglobin in which the iron of heme was oxidized to the ferric form, or methemoglobin. Gibson Q H., *The reduction of methemoglobin in red blood cells and studies on the cause of ideopathic methemoglobinemia*, Biochemical Journal, 42: 13-23, 1948; and, Beutler E., *Methemoglobinemia and other causes of cyanosis*, In Beutler E, Lichtman M A, Coller B W, Kipps T S, eds, Williams Hematology, 5th Edition, New York: McGraw-Hill, pp 654-662, 1994. However, the percent methemoglobin measured was generally low and remained stable throughout the trial, in the range of 2-3%. Hence, degradation of the blood was not observed in these tests.

TABLE

Measurement of gases generated by photolytic activation in flowing blood.

| Time (min) | PH | $pCO_2$ (kPa) | $pO_2$ (kPa) | $SO_2$ (%) | $FO_2Hb$ (%) | FMetHb (%) |
|---|---|---|---|---|---|---|
| 16 | 6.75 | 48.7 | 12.6 | 81.1 | 80.1 | 2.9 |
| 25 | 7.16 | 27.7 | 9.9 | 85.3 | 83.6 | 2.4 |
| 36 | 7.56 | 13.7 | 7.7 | 88.0 | 85.9 | 2.3 |
| 58 | 7.45 | 16.6 | 8.6 | 88.9 | 86.3 | 2.8 |
| 110 | 7.44 | 16.8 | 9.0 | 91.5 | 89.1 | 2.5 |
| 158 | 7.45 | 16.0 | 9.3 | 92.5 | 89.6 | 2.7 |
| 258 | 7.45 | 16.3 | 9.6 | 93.6 | 90.4 | 3.1 |
| 357 | 7.44 | 16.0 | 9.6 | 93.6 | 90.0 | 3.2 |
| 412 | 7.44 | 16.0 | 9.3 | 92.8 | 90.5 | 2.2 |
| 436 | 7.44 | 16.1 | 9.0 | 91.6 | 88.2 | 3.4 |
| 460 | 7.44 | 16.3 | 8.8 | 90.6 | 87.4 | 3.2 |

Blood gas analyses for the Table were made using the NPT7 Blood-Gas Analyzer (Radiometer, Inc). This instrument provided a readout of concentration measurements of the percent oxyhemoglobin ($FO_2Hb$), the saturation of dissolved oxygen in the liquid phase of serum ($SO_2$), the percent methemoglobin (FmetHb), partial pressure of $O_2$ (kPa) and $CO_2$ (kPa), and pH as function of laser illumination in a recirculating blood loop configuration.

The present disclosure applies photolytic principles to the development of a novel respiratory surface which generates an increase in intravascular oxygen and augments oxyhemoglobin formation without the physical delivery of oxygen gas. For the inventive system, a well-characterized semi-conducting metal oxide film was designed as the photo-absorption element, the anatase form of titania, $TiO_2$. Chen F, Xie Y, Zhao J, Lu G., Photocatalytic degradation of dyes on a magnetically separated photocatalyst under visible and UV irradiation, Chemosphere, 44: 1159-1168, 2001; Asahi R, Morikawa T, Ohwaki T, Aoki K, Taga Y., Visible-light photocatalysis in nitrogen-doped titanium oxides, Science, 293: 269-271, 2001; and, Garcia Rodenas L A, Weisz A D, Magaz G E, Blesa M A., Effect of light on the electrokinetic behavior of $TiO_2$ particles in contact with Cr (VI) aqueous solutions, J Colloid Interface Sci, 230: 181-185, 2000. Importantly, the light energy associated with activation by a 354 nm UV laser light selectively excites the electronic transition of the $TiO_2$ semiconductor (350-389 nm band, or at least 3.2 eV), thus resulting in minimal wasted radiation or transmission (and unwanted heating).

As noted earlier, in initial work, Dasse K A, Monzyk B F, Burckle E C, Busch J R, Gilbert R J., *Development of a photolytic artificial lung: Preliminary concept validation*, ASAIO Journal, 2005, it was demonstrated that photoactivation of the proposed thin film in contact with surrogate serum induced the following set of high-yielding reactions within the oxide film, which have now been replicated here with whole blood:

1) UV light is absorbed into the $TiO_2$ layer, thus energizing the material by producing electrical charge separation.
2) Charge separation drives the conversion of water, present in large excess from the serum, to form the "active oxygen" (AO) intermediate in the nanoporous metal oxide film. The use of wavelengths >340 nm was chosen to prevent this active oxygen species from reforming $H_2O$ directly. The solid state configuration results in the physical separation of active oxygen from the red blood cells and blood proteins.
3) Active oxygen spontaneously (and completely) disproportionates directly into $O_2$ as dissolved oxygen, and, in a similarity to photosynthesis, can be facilitated by a $MnO_2$ catalyst film, without forming a gaseous phase.
4) Dissolved oxygen diffuses into the aqueous phase (blood serum), exiting the nanoporosity of the metal oxide film into the flowing blood raising its $SO_2$ value, and is thus available to diffuse into red blood cells.
5) Simultaneously, in order to avoid recombination with active oxygen the freed electrons are conducted away to the cathode and so are available to effect other useful changes. Such recombination would result in the reformation of water, a harmless event except it results in decreased energy efficiency (the "quantum efficiency, $\Phi_{DO}$ value is reduced, where DO=dissolved oxygen) (i.e. the "back reaction").
6) The freed $H^+$ rapidly combines with bicarbonate ions in the serum by a protonation reaction (see above) yielding initially carbonic acid, which is rapidly converted (facilitated by endogenous carbonic anhydrase) into dissolved $CO_2(aq)$, as per normal lung function, ready for elimination (see above reactions). In another embodiment of the disclosure, in some applications it, it appears advantageous to combine these hydrogen ions with the bicarbonate ions using the freed electrons (electrochemical reduction at the cathode) to form a biocompatible organic compound easily eliminated through the urine, the gut, or by other means, or utilized by the body as food, i.e. a reduced sugar. In either case, note that the $H^+$ ions are not required to diffuse from the point of formation, but use the well-known proton "hopping"

mechanism. Voth G A., *The computer simulation of proton transport in biomolecular systems*, Frontiers Bioscience, 8: S1384-1379-1384, 2003. This eliminates another potential diffusion boundary layer.

7) In lieu of $CO_2$ "fixation" (electrochemical reduction) the final step, $CO_2$(aq) is believed to be eliminated by releasing it $CO_2$ gas by perevaporation via a gas selective membrane into the trachea or lung cavity, similar to that done by the natural lung, or through some other blood to air vent route.

In the present disclosure, it is shown that the photolytically-driven artificial lung approach can be used to generate sufficient dissolved oxygen (as a function of unit area and recirculation time) to yield a measurable increase of oxyhemoglobin in flowing whole blood. To determine appropriate upscaling of the disclosed results and to determine desirable dissolved oxygen production rates, the following calculations were performed. Assuming that one molecule of $O_2$ would be formed for every four electrons produced (see above reaction stoichiometry), the measured electrical current was used to calculate that the maximum rate of oxygen generation with the disclosed laboratory scale apparatus is 1.08 mL $O_2/m_2/$min. Projecting this result to an alveolar surface area of 75 $m_2$, as is the case for the human lung, the output of this system would be approximately 81.0 ml $O_2/m_2$/min. This value is a significant fraction of the net oxygen flux traversing the normally functioning pulmonary capillary membrane, that is, 250 ml $O_2/m_2$/min. Since the slow process of liquid dissolution of oxygen gas is not required, a major impediment faced by current artificial lung technologies is avoided. In addition the requirement for natural lung operation of being near gas/solid equilibrium for both air and exhaled $CO_2$, to allow their flow in opposite directions during a breath, is avoided by separating these two components. Instead, owing to the fact that dissolved oxygen flux is not dependent on diffusion across a gas/liquid boundary and against an outflow of diffusing $CO_2$, a high dissolved oxygen flux entering the blood is conceivable with the inventive photolytic process. In addition, the $TiO_2$ semi-conductor material is considerably more durable than PS pigments (i.e., naturally occurring chlorophyll) and, importantly, is selectively excited by light of a narrow UV bandwidth, thus minimizing heat production and the potential exposure of blood cells to UV light. The catalyst film, which converts active oxygen into dissolved oxygen is located within the photoactive film, and buried within the nano-porosity so that oxygen enters water within the nanopores, and only dissolved oxygen exits the surface pores that are exposed to blood.

While the forms of the disclosure herein disclosed constitute presently preferred embodiments, many others are possible. It is not intended herein to mention all of the possible equivalent forms or ramifications of the disclosure. It is to be understood that the terms used herein are merely descriptive, rather than limiting, and that various changes may be made without departing from the spirit of the scope of the disclosure.

The invention claimed is:

1. A process for generating dissolved oxygen in whole blood from a patient comprising:
   a) providing blood from a patient to a photolytic device wherein the photolytic device comprises:
      an inlet for receiving blood from a patient and transporting the blood to a photolytic cell;
      a photolytic cell having a light transparent substrate and a photo-reactive surface, said photo-reactive surface comprising a layer of a light activated, photolytic catalyst and an electrically conductive layer, wherein said photo-reactive surface has the ability to convert water in the blood to dissolved oxygen upon light activation;
      a light source for providing light photons to said light transparent substrate of the photolytic cell and activating said photolytic catalyst to initiate a series of chemical reactions that result in dissolved oxygen generation by the photo-reactive surface of the photolytic cell;
      an outlet for transporting oxygenated blood out of said photolytic cell; and,
   b) returning the oxygenated blood to the patient.

2. The process of claim 1, wherein said light activated, photolytic catalyst is a metal oxide.

3. The process of claim 2, wherein said metal oxide comprises substantially $TiO_2$ (anatase), $WO_3$, ZnO, and combinations thereof.

4. The process of claim 1, wherein said light source is an ultraviolet laser light at 350-390 nm.

5. The process of claim 1, wherein said photolytic cell comprises a transparent substrate and a photolytic coating comprising a first disposed layer of $TiO_2$ (anatase) and a second disposed layer of $MnO_2$.

6. The process of claim 1, wherein said photolytic cell converts water into dissolved oxygen.

7. The process of claim 1, wherein said light-activated photolytic catalyst converts water into active oxygen.

8. The process of claim 1, wherein said light-activated catalyst converts, when photolytically irradiated, water in the blood to hydrogen ions, electrons and active oxygen.

9. The process of claim 8, wherein said active oxygen formed during photolysis is hydrogen peroxide or other forms of oxygen gas precursors.

10. The process of claim 8, wherein said electrons generated during photolysis are then electrically conducted away to avoid reversal of the reaction.

11. Oxygenated whole blood produced by the process of claim 1.

12. The process of claim 1, wherein the whole blood is mammalian whole blood.

13. The process of claim 1, wherein there is an increase in oxyhemoglobin in the oxygenated blood.

14. A process for enhancing the viability of an organ to be transplanted comprising:
   a. providing to an organ to be transplanted whole blood and a photolytic device, wherein the photolytic device comprises:
      i. an inlet for receiving blood from the organ and transplanting the blood to a photolytic cell;
      ii. a photolytic cell having a light transparent substrate and a photo-reactive surface, said photo-reactive surface comprising a layer of light activated, photolytic catalyst and a layer of disproportionation catalyst disposed on said photolytic catalyst and wherein said photo-reactive surface has the ability to convert water in the blood to dissolved oxygen upon light activation;
      iii. a light source for providing light photons to said light transparent substrate of the photolytic cell and activating said photolytic catalyst to initiate a series of chemical reactions that result in dissolved oxygen generation by the photo-reactive surface of the photolytic cell;
      iv. an outlet for transporting oxygenated blood out of said photolytic cell; and,
   b. returning the oxygenated blood to the organ.

15. The process of claim 14, wherein said light activated, photolytic catalyst is a metal oxide.

16. The process of claim 14, wherein said light source is an ultraviolet laser light at 350-390 nm.

17. The process of claim 14, wherein said disproportionation catalyst comprises $MnO_2$.

18. The process of claim 14, wherein said photolytic cell converts water in the whole blood into dissolved oxygen.

19. The process of claim 1, wherein the photo-reactive surface further comprises a layer of a disproportionation catalyst disposed on the photolytic catalyst layer.

20. The process of claim 19 wherein said disproportionation catalyst comprises $MnO_2$.

21. The process of claim 19 wherein said disproportionation catalyst converts active oxygen to dissolved oxygen.

* * * * *